(12) United States Patent
Ren et al.

(10) Patent No.: US 9,883,643 B2
(45) Date of Patent: Feb. 6, 2018

(54) MAIZE CYTOPLASMIC MALE STERILITY (CMS) S-TYPE RESTORER RF3 GENE, MOLECULAR MARKERS AND THEIR USE

(71) Applicant: Dow AgroSciences LLC, Indianapolis, IN (US)

(72) Inventors: Ruihua Ren, Carmel, IN (US); Bruce A. Nagel, Beaver Dam, WI (US); Ryan Gibson, Carmel, IN (US); Yanxin Star Gao, Waunakee, WI (US); Jafar Mammadov, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 190 days.

(21) Appl. No.: 14/586,143

(22) Filed: Dec. 30, 2014

(65) Prior Publication Data
US 2015/0189843 A1    Jul. 9, 2015

Related U.S. Application Data

(60) Provisional application No. 61/922,349, filed on Dec. 31, 2013.

(51) Int. Cl.
| | |
|---|---|
| *A01H 1/02* | (2006.01) |
| *A01H 1/04* | (2006.01) |
| *C12Q 1/68* | (2006.01) |
| *C07K 14/415* | (2006.01) |

(52) U.S. Cl.
CPC ............... *A01H 1/04* (2013.01); *A01H 1/02* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,569,152 | A | 2/1986 | Gracen et al. |
| 5,624,842 | A | 4/1997 | Okuhara et al. |
| 5,644,066 | A | 7/1997 | Sakai et al. |
| 5,981,833 | A | 11/1999 | Wise et al. |
| 6,392,127 | B1 | 5/2002 | Charne et al. |
| 6,951,970 | B2 | 10/2005 | Brown |
| 7,017,375 | B1 | 3/2006 | Chen |
| 7,164,058 | B2 | 1/2007 | Hanson et al. |
| 7,314,971 | B2 | 1/2008 | Brown et al. |
| 7,612,251 | B2 | 11/2009 | Albertsen et al. |
| 2006/0253931 | A1 | 11/2006 | Komori et al. |
| 2012/0090047 | A1 | 4/2012 | Ren et al. |

FOREIGN PATENT DOCUMENTS

| | | |
|---|---|---|
| WO | 1996/30530 | 10/1996 |

OTHER PUBLICATIONS

Frei et al. Crop Science 26: 37-42 (1986).*
Xu et al. Plant Molecular Biology Reporter 27: 511-517 (2009).*
Puchta et al. Trends in Plant Science 1(10): 340-348 (1996).*
Beckett, 1971, Classification of male-sterile cytoplasm in maize (*Zea mays* L), Crop Science, 11: 724-726.
Duvick, 1965, Cytoplasmic pollen sterility in corn, Adv Genet., p. 2-56.
Laughnan and Gabay, 1978, Nuclear and cytoplasmic mutations to fertility in S male-sterile maize, Maize Breeding and Genetics, p. 427-446.
Kamps and Chase, 1997, RFLP mapping of the maize gametophytic restorer-of-fertility locus (rf3) and aberrant pollen transmission of the nonrestoring rf3 allele, Theor Appl Genet, 95: 525-531.
Tie et al., Genome-wide analysis of maize cytoplasmic male sterility-S based on QTL mapping, Plant Mol Biol, 24: 71-80, Mar. 2006.
Zhang et al., 2006, AFLP and PCR-based markers linked to Rf3, a fertility restorer gene for S cytoplasmic male sterility in maize, Mol Gen Genomics, 276: 162-169.
Young and Tanksley, 1989, Restriction fragment length polymorphism maps and the concept of graphical genotypes, Theor Appl Genet, 77(1): 95-101.
Hospital et al, 1992, Using Markers in Gene Introgression Breeding Programs, Genetics, 132: 1199-1210.
Cui et al, 1996, The rf2 Nuclear Restorer Gene of Male-Sterile T-Cytoplasm Maize, Science, 272: 1334-1336.
Liu et al, 2001, Mitochondrial Aldehyde Dehydrogenase Activity is Required for Male Fertility in Maize; Plant Cell, 13: 1063-1078.
Bentolila et al, 2002, A pentatricopeptide repeat-containing gene restores fertility to cytoplasmic male-sterile plants, PNAS, 99: 10887-10892.
Brown et al, 2003, The radish Rfo restorer gene of Ogura cytoplasmic male sterility encodes a protein with multiple pentatricopeptide repeats, Plant Journal, 35: 262-272.
Desloire et al, 2003, Identification of the fertility restoration locus, Rfo, in readish, as a member of the pentatricopeptide-repeat protein family, EMBO, Rep, 4: 588-594.
Koizuka et al, 2003, Genetic characterization of a pentatricopeptide repeat protein gene, orf687, that restores fertility in the cytoplasmic male-sterile Kosena radish, Plant Jour, 34: 407-415.
Klein et al, 2005, Fertility restorer locus Rf1 of sorghum (*Sorghum bicolor* L.) encodes a pentatricopeptide repeat protein not present in the colinear region of rice chromosome 12, Theor Appl Genet, 111: 994-1012.
Kazama and Toriyama, 2003, A pentatricopeptide repeat-containing gene that promotes the processing of aberrant atp6 RNA of cytoplasmic male-sterile rice, FEBS Lett, 544: 99-102.
Akagi et al, 2004, Positional cloning of the rice Rf-1 gene, a restorer of BT-type cytoplasmic male sterility that encodes a mitochondria-targeting PPR protein, Theor Appl Genet, 108(8): 1449-1457.

(Continued)

*Primary Examiner* — David T Fox
(74) *Attorney, Agent, or Firm* — Eric J. Kraus; Barnes & Thornburg LLP

(57) ABSTRACT

The present disclosure provides a method for selecting a plant comprising a functional restorer gene for maize S-type cytoplasmic male sterility comprising the steps of (a) screening a population of plants for at least one marker nucleic acid, wherein the marker nucleic acid comprises an allele linked to the functional restorer gene for maize S-type cytoplasmic male sterility; (b) detecting the marker nucleic acid; (c) identifying a plant comprising the marker nucleic acid; and (d) selecting the plant comprising the marker nucleic acid, wherein the plant comprising the marker nucleic acid further comprises the functional restorer gene for maize S-type cytoplasmic male sterility. The present disclosure also provides methods for restoring fertility in a progeny of an S-type cytoplasmic male sterile plant and methods for transferring an Rf3 gene into a progeny plant.

27 Claims, 2 Drawing Sheets

(56) References Cited

OTHER PUBLICATIONS

Komori et al, 2004, Map-based cloning of a fertility restorer gene, Rf-1, in rice (*Oryza sativa* L.), Plant J, 37: 315-325.
Wang et al, 2006, Cytoplasmic Male Sterility of Rice with Boro II Cytoplasm is Caused by a Cytotoxic Peptide and is Restored by Two Related PPR Motif Genes via Distinct Modes of mRNA Silencing, Plant Cell, 18: 676-687.
Lurin et al, 2004, Genome-Wide Analysis of *Arabidopsis* Pentatricopeptide Repeat Proteins Reveals Their Essential Role in Organelle biogenesis, Plant Cell, 16: 2089-2103.
N. Jensen, 1988, *Plant Breeding Methodology*, John Wiley & Sons, Inc.
Leary et al, 1983, Rapid and sensitive colorimetric method for visualizing biotin-labeled DNA probes hybridized to DNA or RNA immobilized on nitrocellulose: Bio-blots, PNAS, 80: 4045-4049.
Sambrook et al. (ed.), Molecular Cloning: A Laboratory Manual, 2nd ed., vol. 1-3, Cold Spring Harbor Laboratory Press, Cold Spring Harbor, New York, 1989.
Hames and Higgins, *Nucleic Acid Hybridization*, IRL Press, Oxford, 1985.
Tijssen, 1993, *Laboratory Techniques in Biochemistry and Molecular Biology—Hybridization with Nucleic Acid Probes*, Part 1, Chapter 2, Elsevier, NY.
Ausubel et al, 1995, *Current Protocols in Molecular Biology*. Chapter 2, Greene Publishing and Wiley-Interscience, NY.
Tanksley and Orton, 1983, *Isozymes in Plant Breeding and Genetics*, Amsterdam, Elsevier.
Ward et al, 1993, Chemical regulation of transgene expression in plants, Plant Mol Biol, 22: 361-366.
Schena et al, 1991, a steroid-inducible gene expression system for plant cells, PNAS, 88: 10421-10425.
Sachidanandam, 2001, A map of human genome sequence variation containing 1.42 million single nucleotide polymorphisms, Nature, 409: 928-933.
Singleton and Jones, 1930, Heritable characters of maize. XXXV. Male sterile., J. Hered, 21: 266-268.
Eyster, 1931, Heritable characters of maize—male sterile., J. Hered, 22: 99-102.
Beadle, 1932, Genes in Maize for Pollen Sterility, Genetics, 17: 413-431.
Emerson, 1932, A recessive zygotic lethal resulting in 2: 1 ratios for normal vs. male-sterile and colored vs. colorless pericarp in F2 of certain maize hybrids, Science, 75: 566.
Eyster, W.H., 1934, Genetics of *Zea mays*, Bibliographica Genetica, 11: 187-392.
West and Albertsen, 1985, Three new male-sterile genes, MNL, 59: 87.
Loukides et al, 1995, Two new male-sterile mutants of *Zea mays* (Poaceae) with abnormal tapetal cell morphology, Am J Bot, 82: 1017-1023.
Albertsen et al, 1996, Ms-gene designations, MNL, 70: 30-31.
Golubovskaya, 1979, Meiotic mutation in maize, MNL, 53: 66-70.
Trimnell et al, 1998, New chromosome 10S male-sterile mutant: ms29, MNL, 72: 37-38.
Albertsen et al, 1999, Changing a duplicated designation for two different male-sterile mutations, MNL, 73: 48.
Trimnell et al, 1999, New chromosome 9L male-sterile mutants ms35 and ms36, MNL 73: 49-50.
Patterson, 1995, Tests of male sterile mutants, MNL 69: 126-128.
Golubovskaya, 1979, Genetic control of meiosis, Int Rev Cytol, 58: 247-290.
Albertsen et al, 1993, Cloning and Utilizing a Maize Nuclear Male Sterility Gene, Proc Annu Corn Sorghum Ind Res Conf, 48: 224-233.
Trimnell et al, 2002, New chromosome 10 male-sterile mutant: ms49, MNL, 76: 38-39.
Fraley et al, 1983, Expression of bacterial genes in plant cells, PNAS, 80: 4803-4807.
Van den Elzen et al, 1985, A chimaeric hygromycin resistance gene as a selectable marker in plant cells, Plant Mol Biol, 5(5): 299-302.
Hayford et al, 1988, Development of a Plant Transformation Selection System Based on Expression of Genes Encoding Gentamicin Acetyltransferases, Plant Physiol, 86: 1216-1222.
Jones et al, 1987, A dominant nuclear streptomycin resistance marker for plant cell transformation, Mol Gen Genet, 210 (1): 86-91.
Svab et al, 1990, Aminoglycoside-3"-adenyltransferase confers resistance to spectinomycin and streptomycin in *Nicotiana tabacum*, Plant Mol Biol, 14(2): 197-205.
Hille et al, 1986, Bleomycin resistance: a new dominant selectable marker for plant cell transformation, Plant Mol Biol, 7: 171-176.
Comai et al, 1985, Expression in plants of a mutant aroA gene from *Salmonella typhimurium* confers tolerance to glyphosate, Nature, 317: 741-744.
Gordon-Kamm et al, 1990, Transformation of maize cells and regeneration of fertile transgenic plants, Plant Cell, 2: 603-618.
Stalker et al, 1988, Herbicide resistance in transgenic plants expressing a bacterial detoxification gene, Science, 242: 419-423.
Eichholtz et al, 1987, Expression of mouse dihydrofolate reductase gene confers methotrexate resistance in transgenic petunia plants, Somatic Cell Mol Genet, 13(1): 67-76.
Shah et al, 1986, Engineering herbicide tolerance in transgenic plants, Science, 233: 478.
Charest et al, 1990, In vitro study of transgenic tobacco expressing *Arabidopsis* wild type and mutant acetohydroxyacid synthase genes, Plant Cell Rep, 8: 643.
Jefferson, 1987, Assaying chimeric genes in plants: the GUS gene fusion system, Plant Mol Biol Rep, 5: 387-405.
Teeri et al, 1989, Gene fusions to lacZ reveal new expression patterns of chimeric genes in transgenic plants, EMBO J, 8(2): 343-350.
Koncz et al, 1987, Expression and assembly of functional bacterial luciferase in plants, PNAS, 84: 131-135.
DeBlock et al, 1984, Expression of foreign genes in regenerated plants and in their progeny, EMBO, 3: 1681.
Molecular Probes Publication 2908, Imagene Green, p. 1-4., (2001).
Naleway et al, 1991, "Detection of Gus Gene Expression in Transformed Plant Cells With New Lipophilic, Fluorogenic β-Glucuronidase Substrate", J Cell Biol, 115: 151a.
Chalfie et al, 1994, Green fluorescent protein as a marker for gene expression, Science, 263: 802-805.
Myers and Miller, 1988, Optimal alignments in linear space, CABIOS, 4: 11-7.
Smith et al, 1981, Comparison of biosequences, Adv Appl Math, 2: 482-489.
Needleman and Wunsch (1970), A general method applicable to the search for similarities in the amino acid sequence of two proteins, J. Mol. Biol. 48:443-453.
Pearson and Lipman (1988) Proc. Natl. Acad. Sci. U.S.A. 85:2444-2448.
Karlin and Altshcul, 1990, PNAS, 87: 2264-2268.
Karlin and Altschul, 1993, PNAS, 90: 5873-5877.
Mather, 1931, *The Measurement of Linkage in Heredity*, Methuen & Co, London.
Allard, 1956, Formulas and tables to facilitate the calculation of recombination values in heredity, Hilgardia, 24: 235-278.
Van Ooijen et al, 2006, *JoinMap 4: Software for the calculation of genetic linkage maps in experimental populations*, Kyazma BV, Netherlands: Wageningen.
Czechowski et al, 2005, Plant Physiol, 139(1): 5-17.
International Search Report and Written Opinion, International Application No. PCT/US2014/072639, dated Feb. 24, 2015, 11 pages.
Gabay-Laughnan et al., "Molecular-Genetic Characterization of CMS-S Restorer-of-Fertility Alleles Identified in Mexican Maize and Teosinte", Genetics, Feb. 1, 2004, vol. 166, No. 2, pp. 959-970.
Zabala et al., "The nuclear gene Rf3 affects the expression of the mitochondrial chimeric sequence R implicated in S-type male sterility in maize", Genetics, Oct. 1, 1997, vol. 147, Iss. 2, pp. 847-860.

\* cited by examiner

SEQUENCE LISTING

<160> NUMBER OF SEQ ID NOS: 92

<210> SEQ ID NO 1

```
<211> LENGTH: 121
<212> TYPE: DNA
<213> ORGANISM: Zea mays

<400> SEQUENCE: 1
agcgtgaagc caaggctttt cagcctcgtc atagcttcct agctgatgca agaacacagc      60
wcccataagc ctacattcta tttctaccag gcatgggaac aagcaagcac caacgatgaa     120
t                                                                    121

<210> SEQ ID NO 2
<211> LENGTH: 101
<212> TYPE: DNA
<213> ORGANISM: Zea mays

<400> SEQUENCE: 2
tcttgccctg tgctgtcgtg cacataggcc ggggaggaca aggatctttc rtctttagcg      60
agtatcgacc tcaagagagt gttcccggag aagaaggttc c                         101

<210> SEQ ID NO 3
<211> LENGTH: 101
<212> TYPE: DNA
<213> ORGANISM: Zea mays

<400> SEQUENCE: 3
tgtgctaata gcctaacaaa accaagttaa ttataagtcg tttaaataca kcaaagctag      60
gcagctagca atgctaaaaa gttaccacat tattcgttga c                         101

<210> SEQ ID NO 4
<211> LENGTH: 496
<212> TYPE: DNA
<213> ORGANISM: Zea mays

<400> SEQUENCE: 4
caagagagaa agaaaaaaaa tgtcgaacaa gagctgcaaa gaagagaact caccgccgtt      60
gagccagagg acgagaggct tggaggcagg gtcggggggca tcggcctcca cgaagtagta    120
gaacagggcc cgcttgccgc cgccgtcgcc gtccacgccg acgtagccgg agtactggcc    180
gaagctcacc tccggctgcc cggggagccg cgtgatcctg tccgcggcgg ccgcggcggc    240
tgcgcaggaa gccggacggc agagcgcggc cgcgacgagc accagcgcca gcgccagtgg    300
sctggtaatg aaggagctcg ctggagctaa tggcgtggcc atgccgccga tcggccgatg    360
gacagagata gtgtgtgtgt gactggagag ggagagagag agagacaggc gtggaagagt    420
taagtgtgct cttttgcctt gagagcacaa aaaaatagtt tcaaaagctg aatgattcaa    480
cgggacgagg aggagg                                                    496

<210> SEQ ID NO 5
<211> LENGTH: 101
<212> TYPE: DNA
<213> ORGANISM: Zea mays

<400> SEQUENCE: 5
cggcactggc gcccactgct cccgccacgt ccccatcacc accctctttt yacctattcc      60
tgcctccttc ctgctgctca acatccctgc ctgccgggat c                        101

<210> SEQ ID NO 6
<211> LENGTH: 101
<212> TYPE: DNA
```

```
<400> SEQUENCE: 6
ccggactccc gagggctgtg cggcatcgcg atggagccgt cttacccgac yaaaaaaccg    60
gcagggcatg gcggcggcat cgtacaagat ctcggccagg a                       101

<210> SEQ ID NO 7
<211> LENGTH: 101
<212> TYPE: DNA
<213> ORGANISM: Zea mays

<400> SEQUENCE: 7
gcgccgtgtt cagcgggatg gaggcccggt acttcgacct tgtacccggc raaggctggg    60
aggtcgacac cgacagtgtc cgagctctcg ccgacaagaa c                       101

<210> SEQ ID NO 8
<211> LENGTH: 101
<212> TYPE: DNA
<213> ORGANISM: Zea mays

<400> SEQUENCE: 8
aagctgggga acttggattt ctacgcggat cgatccctat acatcggatg kgatttctac    60
gcggatcgaa gagggactgg tttgccgcac gatctagggt a                       101

<210> SEQ ID NO 9
<211> LENGTH: 101
<212> TYPE: DNA
<213> ORGANISM: Zea mays

<400> SEQUENCE: 9
cctagaataa ccacacgaca ccgagcccgg ggttgggagt ggcaaagctg racatgggga    60
cgggtgtgcc aaagggaatc cactcgagtg gatccctcgc c                       101

<210> SEQ ID NO 10
<211> LENGTH: 201
<212> TYPE: DNA
<213> ORGANISM: Zea mays

<400> SEQUENCE: 10
cccgcccccg ccggccaatc actacggcga acgacactat atgtacggaa aggcatagcg    60
aattatatgg ggaagattct caccgttatc agagtggtgt ycgatctggc gatggcgtag   120
cgtgggaccg tggcggagtt gacgctccgg cgatcaattc tgcccgcccc gctcatcaca   180
tcgtcaaatt ggagggagta t                                             201

<210> SEQ ID NO 11
<211> LENGTH: 101
<212> TYPE: DNA
<213> ORGANISM: Zea mays

<400> SEQUENCE: 11
agcaacgggt ggtggtggtg caccggtgcg gtcatggcgc tctccttgct ragcgcgtcg    60
cagaaggtgc gatgcatgag ggtggctggc ggggaggcct a                       101

<210> SEQ ID NO 12
<211> LENGTH: 42
<212> TYPE: DNA
<213> ORGANISM: Artificial Sequence
<220> FEATURE:
<223> OTHER INFORMATION: synthetic oligonucleotide
```

<400> SEQUENCE: 12
gaaggtgacc aagttcatgc tagctgatgc aagaacacag ca                42

<210> SEQ ID NO 13
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 13
gaaggtgacc aagttcatgc ttgaggtcga tactcgctaa agac              44

<210> SEQ ID NO 14
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 14
gaaggtgacc aagttcatgc taaaccaagt taattataag tcgtttaaat acat    54

<210> SEQ ID NO 15
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 15
gaaggtgacc aagttcatgc tagcgagctc cttcattacc agg               43

<210> SEQ ID NO 16
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 16
gaaggtgacc aagttcatgc taggaaggag gcaggaatag gtg               43

<210> SEQ ID NO 17
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 17
gaaggtgacc aagttcatgc tggagccgtc ttacccgacc                   40

<210> SEQ ID NO 18
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 18
gaaggtgacc aagttcatgc ttcgaccttg tacccggcg                    39

<210> SEQ ID NO 19
<211> LENGTH: 42

<212> TYPE: DNA
<213> ORGANISM: Artificial Sequence
<220> FEATURE:
<223> OTHER INFORMATION: synthetic oligonucleotide

<400> SEQUENCE: 19
gaaggtgacc aagttcatgc tcttcgatcc gcgtagaaat cc                42

<210> SEQ ID NO 20
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 20
gaaggtgacc aagttcatgc tggttgggag tggcaaagct ga                42

<210> SEQ ID NO 21
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 21
gaaggtgacc aagttcatgc tcaccgttat cagagtggtg tc                42

<210> SEQ ID NO 22
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 22
gaaggtgacc aagttcatgc tgcaccttct gcgacgcgct t                 41

<210> SEQ ID NO 23
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 23
gaaggtcgga gtcaacggat tctagctgat gcaagaacac agct              44

<210> SEQ ID NO 24
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 24
gaaggtcgga gtcaacggat tcttgaggtc gatactcgct aaagat            46

<210> SEQ ID NO 25
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 25
gaaggtcgga gtcaacggat taaaccaagt taattataag tcgtttaaat acag    54

<210> SEQ ID NO 26
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 26
gaaggtcgga gtcaacggat tagcgagctc cttcattacc agc    43

<210> SEQ ID NO 27
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 27
gaaggtcgga gtcaacggat tcaggaagga ggcaggaata ggta    44

<210> SEQ ID NO 28
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 28
gaaggtcgga gtcaacggat tatggagccg tcttacccga ct    42

<210> SEQ ID NO 29
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 29
gaaggtcgga gtcaacggat tacttcgacc ttgtacccgg ca    42

<210> SEQ ID NO 30
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 30
gaaggtcgga gtcaacggat tctcttcgat ccgcgtagaa atca    44

<210> SEQ ID NO 31
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 31
gaaggtcgga gtcaacggat tggttgggag tggcaaagct gg    42

<210> SEQ ID NO 32
<211> LENGTH: 44
<212> TYPE: DNA
<213> ORGANISM: Artificial Sequence

```
<220> FEATURE:
<223> OTHER INFORMATION: synthetic oligonucleotide

<400> SEQUENCE: 32
gaaggtcgga gtcaacggat tctcaccgtt atcagagtgg tgtt          44

<210> SEQ ID NO 33
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 33
gaaggtcgga gtcaacggat tcaccttctg cgacgcgctc               40

<210> SEQ ID NO 34
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 34
tgcctggtag aaatagaatg taggcttat                           29

<210> SEQ ID NO 35
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 35
gccggggagg acaaggatct tt                                  22

<210> SEQ ID NO 36
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 36
tttttagcat tgctagctgc ctagcttt                            28

<210> SEQ ID NO 37
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 37
caccagcgcc agcgccagt                                      19

<210> SEQ ID NO 38
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 38
cgtccccatc accacctct tt                                   22
```

```
<210> SEQ ID NO 39
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 39
ccgccatgcc ctgccggtt                                                  19

<210> SEQ ID NO 40
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 40
cggtgtcgac ctcccagcct t                                               21

<210> SEQ ID NO 41
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 41
tctacgcgga tcgatccta tacat                                            25

<210> SEQ ID NO 42
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 42
ctttggcaca cccgtcccca t                                               21

<210> SEQ ID NO 43
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 43
cacgctacgc catcgccaga t                                               21

<210> SEQ ID NO 44
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 44
tgcggtcatg gcgctctcct t                                               21

<210> SEQ ID NO 45
<211> LENGTH: 250
<212> TYPE: DNA
<213> ORGANISM: Zea mays

<400> SEQUENCE: 45
```

```
cttgtggata caactttcac caataatcct tgcatgaaca ctcataattt ttgaagtgat    60
gaaacatatt gttgtcccgc acaattatct ccctaccagc aataccagat atgaatttaa   120
aagcscggtg gcaatctaca caaattcgca gattcttcat gatccttata ggtatgccag   180
gtggtataca tatcaatcca aaagccagag caagctttc actgtgttga aacacttctg    240
attctttctc                                                         250
```

```
<210> SEQ ID NO 46
<211> LENGTH: 250
<212> TYPE: DNA
<213> ORGANISM: Zea mays
<220> FEATURE:
<221> NAME/KEY: misc_feature
<222> LOCATION: (125)..(125)
<223> OTHER INFORMATION: InDel [T/-]
<220> FEATURE:
<221> NAME/KEY: misc_feature
<222> LOCATION: (168)..(168)
<223> OTHER INFORMATION: n is a, t, c, or g

<400> SEQUENCE: 46
```

```
ccaccatgga ttttaatccc acctaatcct atccaatcca catgaattaa gatgagaacg    60
aacaggccct taaatggagg caggcaggca ctcaccgctt cttgtcactc atgtccgctc   120
gctttgcgca ggcatgctat tttacccaga gactactgat tgttcttnca tccatcagct   180
gatcccagat ctgtggcatc agtatttcag tgttgtgaat cggccggtgc atgaacttaa   240
tcattaatgc                                                         250
```

```
<210> SEQ ID NO 47
<211> LENGTH: 250
<212> TYPE: DNA
<213> ORGANISM: Zea mays

<400> SEQUENCE: 47
```

```
gttcaagtga gaaattcctc tcgtcaatct tggacaggta agctccagcc ctgactattt    60
cattttcctt tagtaattcc ctgactacat gattcagcaa tcgagaattg ggctcacagc   120
cagcrttctg catggatgaa acatatcttc tgcctcttc caccaatcct tcttttataa    180
gatttgtgat cattatactg taagtcacaa cacwaggcac cagccsactt ctcgagatag   240
aagcaaacag                                                         250
```

```
<210> SEQ ID NO 48
<211> LENGTH: 364
<212> TYPE: DNA
<213> ORGANISM: Zea mays

<400> SEQUENCE: 48
```

```
ggagcttacc tgtccaagat tgacgagagg aatttctcac ttgaacattt aaccgcaatg    60
ttgctggtcg atctcttctc aagcaaagga acttgtaggg aacaaataag atttctccct   120
gcaaagtatc attttcttgc agaggccagt ccgtgattga tatrttgatt tttttttggaa  180 tcagtccttg cacgcacctg tcacagttaa actagtatat gatcttaact aaaaccattg   240
gtttacttca tgttcatgtt tctcggaaga ttttcttctc atttgacctg cttgatatgc   300
agatgttcat ttacttttga tccaatatat gcagagcgtt ttatgttttt cgaagcatat   360
tcgt                                                              364
```

```
<210> SEQ ID NO 49
```

-continued

```
<211> LENGTH: 332
<212> TYPE: DNA
<213> ORGANISM: Zea mays
<220> FEATURE:
<221> NAME/KEY: misc_feature
<222> LOCATION: (165)..(165)
<223> OTHER INFORMATION: InDel [T/-]

<400> SEQUENCE: 49
gtagggaaca aataagattt ctccctgcaa agtatcattt tcttgcagag gccagtccgt      60
gattgatatg ttgatttttt ttggaatcag tccttgcacg cacctgtcac agttaaacta     120
gtatatgatc ttaactaaaa ccattggttt acttcatgtt catgttttct cggaagattt     180
tcttctcatt tgacctgctt gatatgcaga tgttcattta cttttgatcc aatatatgca     240
gagcgtttta tgttttttcga agcatattcg ttccggtgct gatgtagcta tgtgctctcc    300
gtacacaact gatgttgatt ctctcttgta gc                                   332

<210> SEQ ID NO 50
<211> LENGTH: 367
<212> TYPE: DNA
<213> ORGANISM: Zea mays

<400> SEQUENCE: 50
actagtatat gatcttaact aaaaccattg gtttacttca tgttcatgtt tctcggaaga      60
ttttcttctc atttgacctg cttgatatgc agatgttcat ttacttttga tccaatatat     120
gcagagcgtt ttatgttttt cgaagcatat tcgttccggt gctgatgtag ctatgtgctc     180
tccgtrcaca actgatgttg attctctctt gtagcatgtt ttatcatgtc tgttaacaca     240
gccgatgttg catttatgag gaatgacgtt ataactgctg ggagaataat gtagcatgct     300
gaatcctgtt tgggccctg gctgagccgc ccagttcgtc atgaccagca aggtaatgtt     360
catctac                                                               367

<210> SEQ ID NO 51
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 51
gaatttgtgt agattgccac cgc                                              23

<210> SEQ ID NO 52
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 52
gtcactcatg tccgctcgct tt                                               22

<210> SEQ ID NO 53
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 53
agaattgggc tcacagccag ca                                               22
```

<210> SEQ ID NO 54
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 54
agaggccagt ccgtgattga tata                                            24

<210> SEQ ID NO 55
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 55
aaccattggt ttacttcatg ttcatgtttt                                      30

<210> SEQ ID NO 56
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 56
gatgtagcta tgtgctctcc gtg                                             23

<210> SEQ ID NO 57
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 57
gaatttgtgt agattgccac cgg                                             23

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 58
cactcatgtc cgctcgcttg                                                 20

<210> SEQ ID NO 59
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 59
gaattgggct cacagccagc g                                               21

<210> SEQ ID NO 60
<211> LENGTH: 23
<212> TYPE: DNA
<213> ORGANISM: Artificial Sequence
<220> FEATURE:

<223> OTHER INFORMATION: synthetic oligonucleotide

<400> SEQUENCE: 60
gaggccagtc cgtgattgat atg                                       23

<210> SEQ ID NO 61
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 61
ccattggttt acttcatgtt catgtttc                                  28

<210> SEQ ID NO 62
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 62
gatgtagcta tgtgctctcc gta                                       23

<210> SEQ ID NO 63
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 63
ccctaccagc aataccagat atgaattta                                 29

<210> SEQ ID NO 64
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 64
caatcagtag tctctgggta aaatagcat                                 29

<210> SEQ ID NO 65
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 65
gcagaagata tgttttcatc catgcagaa                                 29

<210> SEQ ID NO 66
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 66
gtgcgtgcaa ggactgattc caaaa                                     25

```
<210> SEQ ID NO 67
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 67
gcatatcaag caggtcaaat gagaagaaa                                29

<210> SEQ ID NO 68
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 68
catgctacaa gagagaatca acatcagtt                                29

<210> SEQ ID NO 69
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 69
ggtaagatgg atgatgctat ggaaa                                    25

<210> SEQ ID NO 70
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 70
gcatgtgatc tattcaaaga aatggt                                   26

<210> SEQ ID NO 71
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 71
ggcatgcatc ttgacattgt ttta                                     24

<210> SEQ ID NO 72
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 72
gtcttcaacc ccaataaccc g                                        21

<210> SEQ ID NO 73
<211> LENGTH: 46
<212> TYPE: DNA
<213> ORGANISM: Artificial Sequence
<220> FEATURE:
<223> OTHER INFORMATION: synthetic oligonucleotide
```

<400> SEQUENCE: 73
gaaggtgacc aagttcatgc tgcagatgat ttgctacgga tgatgt          46

<210> SEQ ID NO 74
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 74
gaaggtgacc aagttcatgc taccatggag tgaaaccttta tgtgc          45

<210> SEQ ID NO 75
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 75
gaaggtgacc aagttcatgc tgaaaatggt gatgatccaa gcattcta          48

<210> SEQ ID NO 76
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 76
gcatccatta cccttcccaa          20

<210> SEQ ID NO 77
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 77
aaagggaacc catcaacatg tta          23

<210> SEQ ID NO 78
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 78
gcagcatttc tctgaaaaga ctcaa          25

<210> SEQ ID NO 79
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 79
gggttagttt gggaactcta ttttca          26

<210> SEQ ID NO 80
<211> LENGTH: 45

```
<212> TYPE: DNA
<213> ORGANISM: Artificial Sequence
<220> FEATURE:
<223> OTHER INFORMATION: synthetic oligonucleotide

<400> SEQUENCE: 80
gaaggtcgga gtcaacggat tcagatgatt tgctacggat gatgg            45

<210> SEQ ID NO 81
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 81
gaaggtcgga gtcaacggat taccatggag tgaaacctta tgtgg            45

<210> SEQ ID NO 82
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 82
gaaggtcgga gtcaacggat taaaatggtg atgatccaag cattctg          47

<210> SEQ ID NO 83
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 83
gcgagcagac agctccccct t                                      21

<210> SEQ ID NO 84
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 84
gcagagggca gcaatcactg tcg                                    23

<210> SEQ ID NO 85
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 85
ggtgtttcta ttcttgtcca catcttcat                              29

<210> SEQ ID NO 86
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 86
```

```
gtactcatgg tagtttactg aaagcca                                        27

<210> SEQ ID NO 87
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 87
gcatccatta cccttcccaa t                                              21

<210> SEQ ID NO 88
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 88
atcttgacat tgttttattc agttcg                                         26

<210> SEQ ID NO 89
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 89
ataacgtgcc ttggagtatt tgg                                            23

<210> SEQ ID NO 90
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 90
tggagtgaag cagatgattt gc                                             22

<210> SEQ ID NO 91
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 91
ttgcatccat cttgttgc                                                  18

<210> SEQ ID NO 92
<211> LENGTH: 2445
<212> TYPE: DNA
<213> ORGANISM: Zea mays

<400> SEQUENCE: 92
atgccgtcat gtgcccgcat ctcctccgcc gtctccaccg ccgccgcatc ctcctcctcg     60
ccgccgccgc atcctcctcg ctgccgccgc ctcgccgccg ccacggcgcg cgtgcgggag    120
gggacgctcc gccctgagga agcacacgac ctgctcgacg agttgcagcg tcgaggcacg    180
cccgttctcg agcgcgatct gaacggcttc tcgcggcga tcgcgcgtgc gccgtcctcc    240
gccgcctgca ggagtggccc tgccctcgcc gtcgcgctct tcaaccgcgc ggcgtctcgg    300
```

-continued

```
gctcaaggac cgcgggtgct gtcccccaca tcccacacct acgccatcct catggactgc      360 tgcaccgcg cgcaccgccc agagctagcg ctggcgttct tcggccagct cctcaggaca      420
ggcttgcgcg tcgatatcat catcgctaac caccttctca agggcttttg tgaagcgaag      480
cggacagacg aggctttgga catccttctc cacagaacgc ctgagttggg ctgtgtgccc      540
gatgttttct cgtacagcat acttctgaag agcctctgcg accaaggaaa gagtggccag      600
gcagatgatt tgctacggat gatggctgaa gggggagctg tctgctcgcc cgacgtggtt      660
gcctacaata cagtaatcga cggcttcttt aaggagggtg acgtaaataa agcatgtgat      720
ctattcaaag aaatggtaca gcggggcatt ccacctgatt ttgtgactta tagctctgtg      780
gttcatgccc tgtgtaaggc aagagcaatg gacaaggcag aggcttttcct tcgacaaatg      840 gtcaataaag gtgttctgcc aaataactgg acatataata acttgatata tggatactcc      900
tccacaggac agtggaagga ggcagttagg gtatttaaag aaatgagaag acagagcatc      960
ttaccagatt tgttactttt taacatgttg atgggttccc tttgcaagta tggaaaaatc     1020
aaggaagcta gagatgtttt tgacacaatg gcaatgaagg gccaaaatcc tgatgttttc     1080
tcgtacaata ttatgctcaa cgggtacgct actaaaggat gtctagttga tatgacagat     1140
ctcttcgatt tgatgctagg tgacggtatt gcacctgtca tttgtacttt taatgtgctg     1200
atcaaggcat atgcaaactg tggaatgcta gataaggcta tgatcatctt caatgaaatg     1260
agagaccatg gagtgaaacc taatgtgcta acctatacga cagtgattgc tgccctctgc     1320
agaatcggta gatggatga tgctatgaa aaatttaatc agatgattga tcaaggagta     1380
gcacctgata aatatgcata ccattgcctg attcaaggtt tttgtactca tggtagttta     1440
ctgaaagcca aggaattgat ttcggaaata atgaataatg gcatgcatct tgacattgtt     1500
ttattcagtt cgataattaa caaccttgc aaattgggaa gggtaatgga cgcacaaaat     1560
atatttgact taactgtaaa tgttggtctg catcctactg ctgtggtgta tagtatgctg     1620
atggatgggt actgtcttgt tggcaagatg gagaaagcat taagagtatt tgatgctatg     1680
gtgtcagctg gcattgaacc aaacgatgta gtgtatggta cacttgttaa tggctattgt     1740
aaaattggaa ggattgatga aggattgagt cttttcagag aaatgctgca aagggaata     1800 aagccttcaa ctatttata caacatcata attgatgggt tatttgaggc cgggagaaca     1860
gttcctgcaa aggtgaaatt ccatgaaatg acagaaagtg gtatcgctat gaacaaatgt     1920
acatacagca tagttcttcg tggactttt aaaaatagat gctttgatga agcaatcttt     1980
cttttcaaag aattacgtgc aatgaatgta aagatcgata tcataactct caataccatg     2040
atagctggaa tgtttcaaac caggagagtt gaagaagcta aggatctgtt tgcttctatc     2100
tcgagaagtg ggctggtgcc ttgtgttgtg acttacagta taatgatcac aaatcttata     2160
aaagaaggat tggtggaaga ggcagaagat atgttttcat ccatgcagaa tgctggctgt     2220
gagcccgatt ctcgattgct gaatcatgta gtcaggaat tactaaagaa aaatgaaata     2280
gtcagggctg gagcttacct gtccaagatt gacgagagga atttctcact tgaacattta     2340
accacaatgt tgctggtcga tctcttctca agcaaaggaa cttgtaggga acacataaga     2400
tttctccctg caaagtatca ttttcttgca gaggccagtc cgtga                     2445
```

MAIZE CYTOPLASMIC MALE STERILITY (CMS) S-TYPE RESTORER RF3 GENE, MOLECULAR MARKERS AND THEIR USE

CROSS-REFERENCE TO RELATED APPLICATIONS

This application claims the benefit under 35 USC § 119(e) of U.S. Provisional Application Ser. No. 61/922,349, filed on Dec. 31, 2013, the entire disclosure of which is incorporated herein by reference.

REFERENCE TO SEQUENCE LISTING SUBMITTED ELECTRONICALLY

The official copy of the sequence listing is submitted electronically via EFS-Web as an ASCII formatted sequence listing with a file named "73721_ST25.txt", created on Dec. 30, 2014, and having a size of 25 kilobytes and is filed concurrently with the specification. The sequence listing contained in this ASCII formatted document is part of the specification and is herein incorporated by reference in its entirety.

FIELD OF THE DISCLOSURE

The subject disclosure relates to plant fertility genes. In some embodiments, the disclosure relates to Rf3, a maize restorer of fertility gene. In particular embodiments, the disclosure relates to compositions and methods for restoring fertility to S-type cytoplasmic male sterility (CMS), for example, by using molecular markers linked to, or residing within, the Rf3 gene. Particular embodiments relate to methods for using particular nucleic acid sequences to identify plants that contain restorer of fertility to CMS-S, and methods for hybrid seed production.

BACKGROUND

The development of hybrid plant breeding has allowed for considerable advances in quality and quantity of crops that are produced. Increased yield and the combination of desirable characteristics, such as resistance to disease and insects, heat and drought tolerance, and variations in plant composition are all possible, in part, due to hybridization procedures. Hybridization procedures rely on the contribution of pollen from a male parent plant to a female parent plant in order to produce resulting hybrids.

Plants may self-pollinate if pollen from one flower is transferred to the same or a different flower of the same plant. Alternatively, plants may cross-pollinate if the pollen originates in a flower from a different plant. Maize plants (Zea mays) may be bred using both self-pollination and cross-pollination techniques. Maize plants have male flowers, which are located on the tassel, and female flowers, which are located on the ear of the same plant. Natural pollination in maize occurs when pollen from the tassels reaches the silks that are found at the tops of the incipient ears. Importantly, the development of maize hybrids relies upon male sterility systems.

The development of maize hybrids requires the development of homozygous inbred lines, the crossing of these lines, and the evaluation of the resultant crosses. Pedigree breeding and recurrent selection are two breeding methods that may be used to develop inbred lines from maize populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics absent in one, or complementing the other. The new inbred plants are crossed with other inbred lines and the resultant hybrids from these crosses are evaluated to determine which are more desirable. The hybrid progeny from the first generation are designated $F_1$. In the development of hybrids, only the $F_1$ hybrids are sought. The $F_1$ hybrid is typically more vigorous than its inbred parents. This hybrid vigor, termed "heterosis," typically leads to more desirable traits, for example, increased vegetative growth and increased yield.

Hybrid maize seed can be produced by a male sterility system incorporating manual detasseling. To produce hybrid seed, the tassel is removed from the growing female inbred parent, which can be proximately planted in various alternating row patterns with the male inbred parent. Consequently, provided that there is sufficient isolation from foreign maize pollen, the ears of the female inbred will be fertilized only with pollen from the male inbred. The resulting seed is termed hybrid $F_1$ seed.

However, manual detasseling is labor-intensive and costly. Manual detasseling is also often ineffective because in some instances environmental variation in plant development can result in plants tasseling after manual detasseling of the female parent plant is completed or because a detasseler might not completely remove the tassel of a female inbred plant. If detasseling is ineffective, the female plant will successfully shed pollen and some female plants will be self-pollinated. This will result in seed of the female inbred being undesirably harvested along with the hybrid seed which is normally produced. Female inbred seed is not as productive as $F_1$ seed. In addition, the presence of female inbred seed can represent a germplasm security risk for the producer of the hybrid seed.

A female inbred plant can also be mechanically detasseled by a machine. Mechanical detasseling is approximately as reliable as hand detasseling, but is faster and less expensive. However, most detasseling machines produces more damage to the plants than hand detasseling. Thus, neither manual nor mechanical detasseling is entirely satisfactory at the present time.

Genetic male sterility is an alternative method that may be advantageously used in hybrid seed production. The laborious detasseling process can desirably be avoided in some genotypes by using cytoplasmic male-sterile inbred plants. In the absence of a fertility restorer gene, plants of a cytoplasmic male-sterile inbred are male sterile as a result of factors resulting from the cytoplasmic, as opposed to the nuclear, genome. Therefore, the characteristic of male sterility is inherited exclusively through the female parent in maize plants, since only the female provides cytoplasm to the fertilized seed. Cytoplasmic male-sterile plants are fertilized with pollen from another inbred plant that is not male-sterile. Pollen from the second inbred plant may or may not contribute genes that make the hybrid plants male-fertile. Typically, seed from detasseled normal maize and cytoplasmic male-sterile-produced seed of the same hybrid must be blended to ensure that adequate pollen loads are available for fertilization when the hybrid plants are grown and to ensure cytoplasmic diversity.

Drawbacks to use of cytoplasmic male sterility (CMS) as a system for the production of hybrid seed include the association of specific variants to CMS with susceptibility to certain crop diseases. See, e.g., Beckett (1971) Crop Science 11:724-6. This problem has specifically discouraged the use of the CMS-T variant in the production of hybrid maize seed, and has had a negative impact on the use of CMS in maize in general.

Cytoplasmic male sterility is the maternally inherited inability to produce functional pollen. More than 40 sources of CMS have been found and classified into three major groups by differential fertility restoration reactions. These groups are designated as CMS-T (Texas), CMS-S (USDA), and CMS-S (Charrua) (Beckett, 1971). In the CMS-T group, two dominant genes, Rf1 and Rf2, which are located on chromosomes 3 and 9, respectively, are required for the restoration of pollen fertility (Duvick, 1965). The S-cytoplasm is restored by a single gene, Rf3, which has been mapped on chromosome 2 (Laughnan and Gabay, 1978).

In maize, the restorer of the S type of CMS behaves as a gametophytic trait. Maize plants with S cytoplasm are restored by the single dominant gene, Rf3, which was mapped to the long arm of chromosome 2 and located between the whp1 and bnl17.14 loci (Kamps and Chase, 1997). Tie (2006) reported that Rf3 was associated with SSR markers umc1525 and bnl1g1520 at distances of 2.3 and 8.9 cM, respectively. Zhang et al. (2006) identified three amplified fragment length polymorphism markers that were tightly linked to the Rf3 gene.

Heterozygous (Rf3/rf3) CMS-S plants are semi-fertile, shedding approximately 50% abortive collapsed pollen containing the rf3 allele and 50% starch-filled fertile pollen containing the Rf3 allele. The rf3 allele in Rf3/rf3 plants cannot be transferred to progeny through sterile pollen, thus generating sterile plants in F2 generation (Tie et al., 2006). This type of inheritance makes it very difficult to collect accurate phenotypic data from an F2 mapping population. Traditional methods for identifying mutations are labor and time-intensive, whole-genome sequencing was considered as an approach to determine the differences between CMS-S and restorer lines. At the same time, a backcross 1 (BC1) mapping population was designed to evaluate the identified mutations. A BC1 mapping population is advantageously more useful to evaluate phenotypes. Individuals from a backcross population have either Rf3/rf3 or rf3/rf3 genotypes, and thus there is no need to distinguish fully fertile phenotype from partially fertile phenotype during the phenotyping process.

Molecular markers are particularly useful for accelerating the process of introducing a gene or quantitative trait loci (QTL) into an elite cultivar or breeding line via backcrossing. Markers linked to the gene can be used to select plants possessing the desired trait, and markers throughout the genome can be used to select plants that are genetically similar to the recurrent parent (Young and Tanksley (1989) Theor. Appl. Genet. 77:95-101; Hospital et al. (1992) Genetics 132:1199-210).

Most of the plant fertility restorer genes have been cloned via a map-based cloning strategy. To date, five restorer genes have been isolated from several plant species including maize (*Zea Mays* L.) (Cui et al. (1996) Science 272:1334-6; Liu et al. (2001) Plant Cell 13:1063-78), petunia (*Petunia hybrida*) (Bentolila et al. (2002) Proc. Natl. Acad. Sci. USA 99:10887-92, radish (*Raphanus sativus* L.) (Brown et al. (2003) Plant J. 35:262-72; Desloire et al. (2003) EMBO Rep. 4:1-7; Koizuka et al. (2003) Plant J. 34:407-15), sorghum (*Sorghum bicolor* L.) (Klein et al. (2005) Theor. Appl. Genet. 111:994-1012) and rice (*Oryza sativa* L.) (Kazama and Toriyama (2003) FEBS Lett. 544:99-102; Akagi et al. (2004) Theor. Appl. Genet. 108:1449-57; Komori et al. (2004) Plant J. 37:315-25; Wang et al. (2006) Plant Cell 18:676-87. All of the identified restorer genes, except for Rf2 in maize, encode different pentatricopeptide repeat (PPR) proteins. The PPR protein contains 2 to 27 repeats of 35 amino acids, referred to as PPR motifs (Small and Peeters, 2000). Many PPR proteins are targeted to mitochondria where the CMS-associated genes and products are located (Lurin et al., 2004).

Additional information regarding fertility restorer genes from maize, rice, petunia, and radish may be found in U.S. Patent Application Ser. No. US2006/0253931, and in U.S. Pat. Nos. 5,981,833; 5,624,842; 4,569,152; 6,951,970; 6,392,127; 7,612,251; 7,314,971; 7,017,375; 7,164,058; and 5,644,066, all of which are incorporated herein by reference.

BRIEF SUMMARY OF THE DISCLOSURE

In some embodiments, the present disclosure provides a method for selecting a plant comprising a functional restorer gene for maize S-type cytoplasmic male sterility. The method comprises the steps of (a) screening a population of plants for at least one marker nucleic acid, wherein the marker nucleic acid comprises an allele linked to the functional restorer gene for maize S-type cytoplasmic male sterility; (b) detecting the marker nucleic acid; (c) identifying a plant comprising the marker nucleic acid; and (d) selecting the plant comprising the marker nucleic acid, wherein the plant comprising the marker nucleic acid further comprises the functional restorer gene for maize S-type cytoplasmic male sterility.

In other embodiments, the present disclosure provides a method for restoring fertility in a progeny of an S-type cytoplasmic male sterile plant. The method comprises the steps of (a) crossing a female plant with a male plant to generate a population of progeny plants, wherein the female plant is an S-type cytoplasmic male sterile plant, and wherein the male plant possesses a functional restorer gene for S-type cytoplasmic male sterility; (b) screening the population of progeny plants to identify a fertile progeny plant comprising at least one marker nucleic acid comprising an allele linked to the functional restorer gene for maize S-type cytoplasmic male sterility; (c) selecting the fertile progeny plant comprising at least one marker nucleic acid comprising an allele linked to the functional restorer gene for maize S-type cytoplasmic male sterility; and (d) propagating the fertile progeny plant, wherein the fertile progeny plant comprises the functional restorer gene for maize S-type cytoplasmic male sterility.

In some embodiments, the present disclosure provides a method for transferring an Rf3 gene into a progeny plant. The method comprises the steps of (a) crossing a first parent plant and a second parent plant to produce a progeny plant, wherein at least one parent plant comprises the Rf3 gene; (b) analyzing the progeny plant for the presence of at least one marker that is linked to the Rf3 gene to obtain an Rf3 progeny plant; (c) backcrossing the Rf3 progeny plant with either the first parent plant or the second parent plant to produce a next-generation progeny plant; and (d) analyzing the next-generation progeny plant for the presence of the at least one marker that is linked to the Rf3 gene to obtain an Rf3 next-generation progeny plant.

SEQUENCE LISTING

Figure 1A:
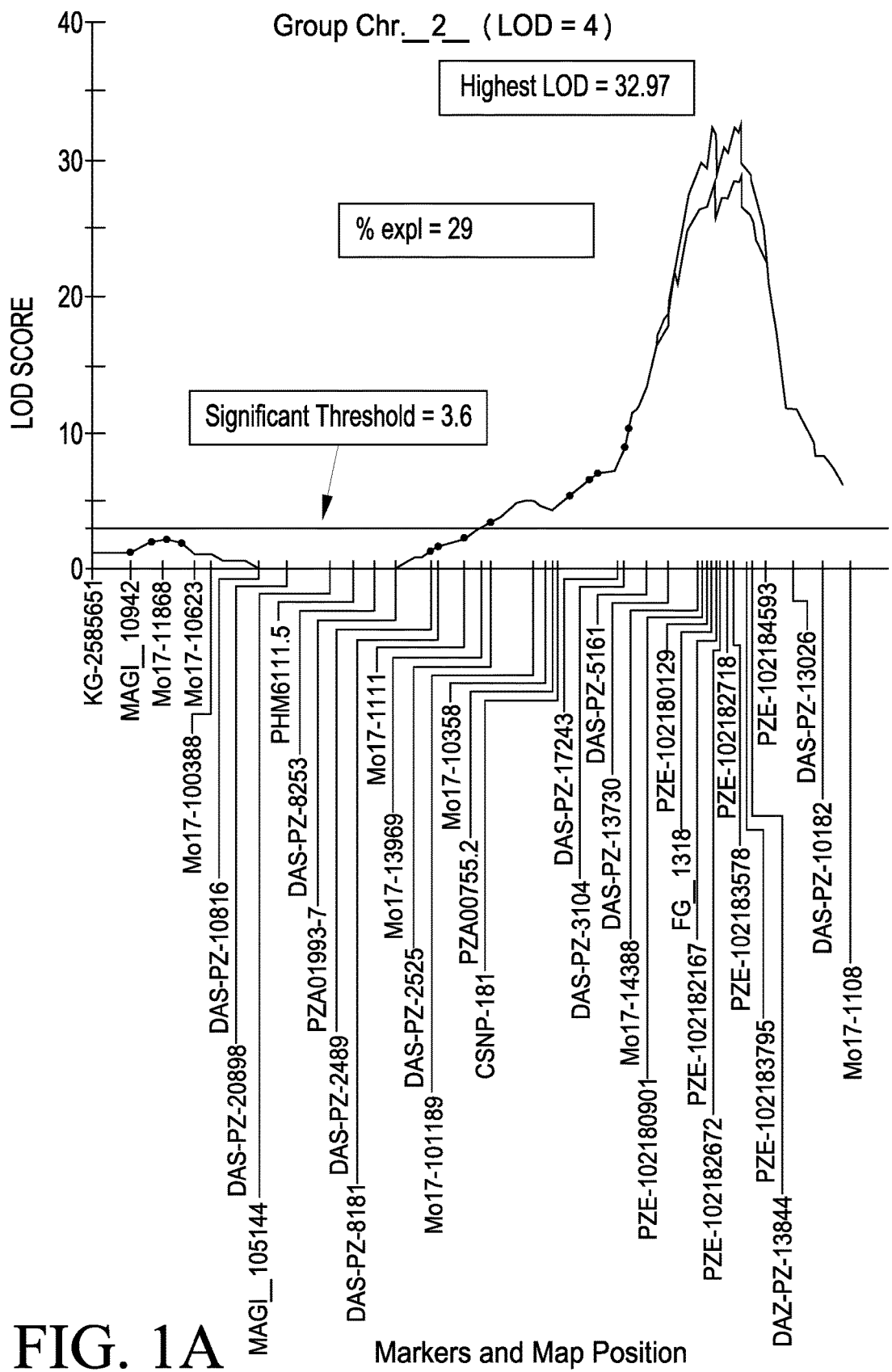
FIG. 1A is a QTL plot showing the LOD scores of markers associated with the CMS-S fertility restorer QTL.

SEQ ID NOs:1-44 show exemplary sequences of markers and primers that are linked (e.g., linked; tightly linked; or extremely tightly linked) to the maize Rf3 gene and are within the 8.3 Mb region on chromosome 2 that contains the Rf3 locus.

SEQ ID NOs:45-68 show exemplary sequences of polymorphic markers and primers developed from several PPR genes.

SEQ ID NOs: 69-85 show exemplary sequences of polymorphic markers and primers developed from the PPR2 gene.

SEQ ID NOs: 86-91 show exemplary sequences of primers and probes for the Rf3 allele specific TaqMan® assay and the internal control, Elongation Factor α-1.

SEQ ID NO:92 is a cDNA sequence for the Mo17 Rf3-PPR2 gene (*Zea mays* cultivar S-Mo17(Rf3/Rf3) PPR-814a mRNA, complete cds; Sequence ID: gb|FJ176574.1).

DETAILED DESCRIPTION

I. Terms

Backcrossing: Backcrossing methods may be used to introduce a nucleic acid sequence into a plant. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the nonrecurrent parent.

Linked, tightly linked, and extremely tightly linked: As used herein, linkage between genes or markers refers to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term "linked" may also refer herein to one or more genes or markers that are located within about 8.5 Mb of one another on the same maize chromosome.

Thus, two "linked" genes or markers may be separated by about 8.5 Mb; 8.3 Mb; 8.0 Mb; 7.5 Mb; 7.0 Mb; 6.5 Mb; 6.0 Mb; 5.5 Mb; 5.0 Mb; 4.5 Mb; 4.0 Mb; 3.5 Mb; 3.0 Mb; 2.5 Mb; 2.0 Mb; about 1.95 Mb; about 1.9 Mb; about 1.85 Mb; about 1.8 Mb; about 1.75 Mb; about 1.7 Mb; about 1.65 Mb; about 1.6 Mb; about 1.55 Mb; about 1.5 Mb; about 1.45 Mb; about 1.4 Mb; about 1.35 Mb; about 1.3 Mb; about 1.25 Mb; about 1.2 Mb; about 1.15 Mb; about 1.1 Mb; about 1.05 Mb; about 1.0 Mb; about 0.95 Mb; about 0.9 Mb; about 0.85 Mb; about 0.8 Mb; about 0.75 Mb; about 0.7 Mb; about 0.65 Mb; about 0.6 Mb; about 0.55 Mb; about 0.5 Mb; about 0.45 Mb; about 0.4 Mb; about 0.35 Mb; about 0.3 Mb; about 0.25 Mb; about 0.2 Mb; about 0.15 Mb; about 0.1 Mb; about 0.05 Mb; about 0.025 Mb; and about 0.01 Mb. Particular examples of markers that are "linked" to Rf3 include nucleotide sequences on the long arm of chromosome 2 of the maize genome, e.g., Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39.

As used herein, the term "tightly linked" may refer to one or more genes or markers that are located within about 0.5 Mb of one another on the same maize chromosome. Thus, two "tightly linked" genes or markers may be separated by about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.1 Mb; and about 0.05 Mb. Particular examples of markers that are "tightly linked" to Rf3 include PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39.

As used herein, the term "extremely tightly linked" may refer to one or more genes or markers that are located within about 100 kb of one another on the same maize chromosome. Thus, two "extremely tightly linked" genes or markers may be separated by about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb; about 30 kb; about 25 kb; about 20 kb; about 15 kb; about 10 kb; about 5 kb; and about 1 kb. Particular examples of markers that are "extremely tightly linked" to Rf3 include CMSS03, CMSS10, CMSS15, CMSS34, DASCMS-SRf31, DASCMS-SRf34, DASCMS-SRf321, and DASCMS-SRf39.

Linked, tightly linked, and extremely tightly genetic markers of Rf3 may be useful in marker-assisted breeding programs to identify restorer for maize S-type cytoplasmic male sterility gene types, and to breed this trait into maize varieties.

Locus: As used herein, the term "locus" refers to a position on the genome that corresponds to a measurable characteristic (e.g., a trait). A SNP locus is defined by a probe that hybridizes to DNA contained within the locus.

Marker: As used herein, the term "marker" refers to a gene or nucleotide sequence that can be used to identify plants having a particular allele, e.g., Rf3. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). The term "marker allele" refers to the version of the marker that is present in a particular plant.

The term marker as used herein may refer to a cloned segment of maize chromosomal DNA (for example, as defined by Mo17-14388, PZE-102180901, PZE-102180129, FG-1318, PZE-102182167, PZE-102182672, PZE-102182718, PZE-102183578, PZE-102183795, DAS-PZ- 13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39), and may also or alternatively refer to a DNA molecule that is complementary to a cloned segment of maize chromosomal DNA (for example, DNA complementary to Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39).

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the maize genome. This is referred to herein as a "contiguous probe." The additional, contiguous nucleotide sequence is referred to as "upstream" or "downstream" of the original marker, depending on whether the contiguous nucleotide sequence from the maize chromosome is on the 5' or the 3' side of the original marker, as conventionally understood. The additional, contiguous nucleotide sequence may be located between the original marker and the 8.3 Mb region on chromosome 2 of the maize genome that is located between flanking markers Mo17-14388 and PZE-102184593. As is recognized by those of ordinary skill in the art, the process of obtaining additional, contiguous nucleotide sequence for inclusion in a marker may be repeated nearly indefinitely (limited only by the length of the chromosome), thereby identifying additional markers along the maize chromosome. Any of the above-described markers may be used in some embodiments of the present disclosure.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: Radiolabeling by nick translation; random priming; tailing with terminal deoxytransferase; or the like, where the nucleotides employed are labeled, for example, with radioactive $^{32}$P. Other labels which may be used include, for example and without limitation: fluorophores; enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the maize genome so that the noncontiguous probe is genetically linked to the same gene (e.g., Rf3). For example, in some embodiments, a noncontiguous probe can be located within 500 kb; 450 kb; 400 kb; 350 kb; 300 kb; 250 kb; 200 kb; 150 kb; 125 kb; 100 kb; 0.9 kb; 0.8 kb; 0.7 kb; 0.6 kb; 0.5 kb; 0.4 kb; 0.3 kb; 0.2 kb; or 0.1 kb of the original marker on the maize genome.

In an embodiment, a probe may be an exact copy of a marker to be detected. A probe may also be a nucleic acid molecule comprising, or consisting of, a nucleotide sequence which is substantially identical to a cloned segment of maize chromosomal DNA (for example, as defined by Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39). As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence.

In an embodiment, a probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ and/or Mg$^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, the term "stringent conditions" encompasses conditions under which hybridization will only occur if there is less than 25% mismatch between the hybridization molecule and the DNA target. Stringent conditions include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions include hybridization at 65° C. in 6× saline-sodium citrate (SSC) buffer, 5×Denhardt's solution, 0.5% SDS, and 100 µg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

With respect to all probes discussed, supra, the probe may comprise additional nucleic acid sequences, for example: gDNA; promoters; transcription signals; and/or vector sequences. Any of the probes discussed, supra, may be used to define additional markers that are linked to a gene involved in restoring fertility to S-type cytoplasmic sterile maize (e.g., Rf3). Markers thus identified may be equivalent to exemplary markers named in the present disclosure and, thus, are within the scope of the present disclosure.

Marker-assisted breeding: As used herein, the term "marker-assisted breeding" may refer to an approach to breeding directly for one or more complex traits (e.g., CMS-S restorer of fertility). In practice, plant breeders attempt to identify readily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, eliminating the need to maintain plants to maturity; and co-dominance of the isozyme marker alleles allows discrimination between homozygotes and heterozygotes. See Rick (1983) in Tanksley and Orton, supra.

Operably linked: A first nucleotide sequence is "operably linked" with a second nucleic acid sequence when the first nucleic acid sequence is in a functional relationship with the second nucleic acid sequence. For example, a promoter is operably linked to a coding sequence if the promoter affects the transcription or expression of the coding sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

Promoter: As used herein, the term "promoter" refers to a region of DNA that may be upstream from the start of transcription, and that may be involved in recognition and binding of RNA polymerase and other proteins to initiate transcription. A promoter may be operably linked to a gene for expression in a cell, or a promoter may be operably linked to a nucleotide sequence encoding a signal sequence which may be operably linked to a gene for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions or the presence of light. Tissue-specific, tissue-preferred, cell type specific, and inducible promoters constitute the class of "non-constitutive" promoters. A "constitutive" promoter is a promoter which may be active under most environmental conditions.

Any inducible promoter can be used in some embodiments of the present disclosure. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that responds to copper; 1n2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: promoters from plant viruses, such as the 35S promoter from CaMV; promoters from rice actin genes; ubiquitin promoters; pEMU; MAS; maize H3 histone promoter; and the ALS promoter, Xba1/NcoI fragment 5' to the *Brassica napus* ALS3 structural gene (or a nucleotide sequence similarity to said Xba1/NcoI fragment) (see, e.g., WO 96/30530).

Any tissue-specific or tissue-preferred promoter may also be utilized in some embodiments the present disclosure. Plants transformed with a gene operably linked to a tissue-specific promoter may produce the protein product of the transgene exclusively, or preferentially, in a specific tissue. Exemplary tissue-specific or tissue-preferred promoters include, but are not limited to: a root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Sequence identity: The terms "sequence identity" or "identity," as used herein in the context of two nucleic acid or polypeptide sequences, may refer to the residues in the two sequences that are the same when aligned for maximum correspondence over a specified comparison window.

When percentage of sequence identity is used in reference to proteins, it is recognized that residue positions which are not identical often differ by conservative amino acid substitutions, where amino acid residues are substituted for other amino acid residues with similar chemical properties (e.g., charge, hydrophobicity, or steric effects), and therefore do not change the functional properties of the molecule.

Therefore, when sequences differ by conservative substitutions, the percent sequence identity may be adjusted upwards to correct for the conservative nature of the substitution at the site of the non-identical residue. Sequences that differ by such conservative substitutions are said to have "sequence similarity" or "similarity." Techniques for making this adjustment are well known to those of ordinary skill in the art. Typically, such techniques involve scoring a conservative substitution as a partial, rather than a full, mismatch, thereby increasing the percentage sequence identity. For example, where an identical amino acid is given a score between 0 and 1, and a non-conservative substitution is given a score of 0, a conservative substitution is given a score between 0 and 1. The scoring of conservative substitutions may be calculated, for example, as implemented in the program PC/GENE (Intelligenetics, Mountain View, Calif.).

As used herein, the term "percentage of sequence identity" may refer to the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Single-nucleotide polymorphism (SNP): As used herein, the term "single-nucleotide polymorphism" may refer to a DNA sequence variation occurring when a single nucleotide in the genome (or other shared sequence) differs between members of a species or paired chromosomes in an individual.

Within a population, SNPs can be assigned a minor allele frequency the lowest allele frequency at a locus that is observed in a particular population. This is simply the lesser of the two allele frequencies for single-nucleotide polymorphisms. There are variations between human populations, so a SNP allele that is common in one geographical or ethnic group may be much rarer in another.

Single nucleotide polymorphisms may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed "synonymous" (sometimes referred to a silent mutation). If a different polypeptide sequence is produced, they are termed "non-synonymous." A non-synonymous change may either be missense or nonsense, where a missense change results in a different amino acid and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) Nature 409:928-33.

Trait or phenotype: The terms "trait" and "phenotype" are used interchangeably herein. For the purposes of the present disclosure, a trait of particular interest is fertility restoration of S-type CMS.

II. The Rf3 Gene and Molecular Markers Thereof

The present disclosure provides particular embodiments of a gene impacting male fertility in plants, maize Rf3, and linked genetic markers thereof, which can be useful in a variety of systems to control male fertility. Furthermore, the polymorphism inherent in the disclosed linked genetic markers allows a plant breeder to follow the particular allele of the gene, Rf3 or rf3, in a segregating population.

The Rf3 gene was initially mapped to chromosome 2 in an F2 population of 450 individuals derived from a cross of a male sterile line '4XP811-D' with a restoring line 'LH60.' In view of the practical importance of cytoplasmic male sterility and pollen fertility restoration in maize hybrid seed production, and of the necessity of cytoplasm source diversification, fine mapping of the maize Rf3 restorer gene for CMS-S to a very small region by using molecular markers with a KASPar™ genotyping technique and the identification of the maize Rf3 gene through map-based cloning are described. It was determined that Rf3 is a single dominant restorer gene for CMS-S in two maize inbreds: LH60 and MBB56.

The Rf3 gene encodes a pentatricopeptide repeat (PPR) protein, as do nearly all other fertility restorer genes. The identification of the Rf3 gene and Rf3 gene markers may greatly facilitate the development and deployment of the CMS-S fertility restoration trait broadly in plant germplasm. In some embodiments, markers that are linked to (e.g., linked; tightly linked; or extremely tightly linked) or reside within the maize Rf3 gene, or the maize Rf3 gene sequence itself, may be used to introduce the maize Rf3 gene into plant organisms.

Rf3 was mapped using SNP markers to a region of approximately 8.3 Mb interval by flanked markers Mo17-14388 and DAS-PZ-13844 on the long arm of chromosome 2. Annotation of this interval with reference genome sequence from Zea mays c.v. B73 revealed 10 PPR genes and further fine-mapped Rf3 gene to a small interval of approximately 1.3 Mb.

In the present disclosure, molecular markers that are linked to the maize CMS-S restorer gene, Rf3, are provided. DNA segments containing sequences involved in restoration of fertility to CMS-S plants are identified. These segments are located between markers that are linked to the Rf3 gene (SEQ ID NO:92). Nucleic acid molecules comprising the Rf3 gene are also provided. The segments identified, and the markers thereof, are described herein, in part, by their position in a particular region on the long arm of maize chromosome 2.

The position of the segments identified, and the markers thereof, when expressed as recombination frequencies or map units, are provided herein as a matter of general information. The embodiments described herein were obtained using a maize population, 4XP811-DxLH60. However, the positions of particular segments and markers as map units are expressed with reference to the publically available B73 maize inbred genome sequence (B73 RefGen v2), which may be found at Maize GDB. It is expected that numbers given for particular segments and markers as map units may vary from cultivar to cultivar and are not part of the essential definition of the DNA segments and markers, which DNA segments and markers are otherwise described, for example, by nucleotide sequence.

The dominant allele of the Rf3 gene controls fertility restoration in the CMS-S/Rf3 system. In particular embodiments, an Rf3 gene is provided (SEQ ID NO:92). In some embodiments, the present disclosure also includes those nucleotide sequences which are substantially identical to the Rf3 sequence (SEQ ID NO:92). For example, in some embodiments, a nucleic acid molecule is an Rf3 homologue that is at least about 85% identical to the Rf3 sequence (SEQ ID NO:92). An Rf3 homologue may be 86%; 87%; 88%; 89%; 90%; 91%; 92%; 93%; 94%; 95%; 96%; 97%; 98%; 99% or 99.5% identical to the Rf3 sequence (SEQ ID NO:92). Such an Rf3 homologue may be readily identified and isolated from any complete or partial genomes readily available to those of skill in the art for a variety of organisms.

Some embodiments also include functional variants of the Rf3 gene. Functional variants of Rf3 include, for example, the Rf3 sequence (SEQ ID NO:92) comprising one or more nucleotide substitutions, deletions, or insertions, wherein the functional variant restores male fertility to CMS-S corn, as may be measured by routine techniques well-known to those of ordinary skill in the art. For example, the capability of a particular variant of the Rf3 gene to restore male fertility to CMS-S corn may be determined by routine introduction of the mutation or fragment into plants homozygous for a sterile rf3 allele, followed by routine observation of the plant for male sterility. Functional variants of the Rf3 gene may be created by site-directed mutagenesis, induced mutation, or they may occur as allelic variants (polymorphisms, e.g., SNPs).

In some embodiments, therefore, functional variants of the Rf3 gene may be mutations of Rf3, or fragments smaller than entire sequence of Rf3, which retain the male sterility controlling properties of the Rf3 gene. Such mutations and fragments are therefore considered to be within the scope of the subject disclosure. One of ordinary skill in the art can readily determine whether a mutation or fragment of the Rf3 sequence set forth herein retains the properties of the Rf3 gene.

III. Methods of Using the Rf3 Gene

The Rf3 gene described herein may be used via techniques known by one of skill in the art to manipulate a gene to cause a desired effect. For example and without limitation, the Rf3 gene may be used: to introduce a mutant Rf3 sequence into a plant to cause sterility; to introduce a mutation into the native Rf3 sequence; to introduce an antisense nucleic acid molecule targeting Rf3 DNA or RNA into a plant to affect fertility; to use hairpin formations; or to link Rf3 sequence(s) with other nucleic acid sequences to control the expression of Rf3 gene product. For example, in some embodiments, the Rf3 gene (SEQ ID NO:92) may be used to facilitate the utilization of the CMS-S/Rf3 male fertility system in conjunction with other genes or mutants impacting male fertility in maize.

In some embodiments, the Rf3 gene may be introduced into a maize plant that is suitable for use in a male fertility system other than the CMS-S/Rf3 male fertility system. Alternatively, a gene or mutant gene other than Rf3 may be introduced into a maize plant that is suitable for use in the CMS-S/Rf3 male fertility system, such that the introduced gene or mutant gene may be used to provide additional or complementary fertility control. Specific examples of other male fertility genes and mutations in maize include: CMS-T/Rf1; CMS-T/Rf2; CMS-S/Rf3; ms1 (Singleton and Jones (1930) J. Hered. 21:266-8); ms2 and ms3 (Eyster (1931) J. Hered. 22:99-102); mss, ms7, ms8, ms9, ms10, ms11, ms12, ms13, and ms14 (Beadle (1932) Genetics 17:413-31); ms17 (Emerson (1932) Science 75:566); ms20 (Eyster (1934) Bibliographia Genetica 11:187-392); ms23 and ms24 (West and Albertsen (1985) MNL 59:87); ms25 and ms26 (Loukides et al. (1995) Am. J. Bot. 82:1017-23); ms27 and ms38 (Albertsen et al. (1996) MNL 70:30-1); ms28 (Golubovskaya (1979) MNL 53:66-70); ms29 and ms31 (Trimnell et al. (1998) MNL 72:37-38); ms30 (Albertsen et al. (1999) MNL 73:48); ms32, ms36, and ms37 (Trimnell et al. (1999) MNL 73:48-50); ms33 and ms34 (Patterson (1995) MNL 69:126-8); ms43 (Golubovskaya (1979) Int. Rev. Cytol. 58:247-90); ms45 (Albertsen et al. (1993) Proc. Annu. Corn Sorghum Ind. Res. Conf. 48:224-33; and ms48, ms49, and ms50 (Trimnell et al. (2002) MNL 76:38-9).

When a nucleic acid sequence (e.g., Rf3) is "introduced" into an organism, such as a plant, the technique or methodology used for the introduction of a nucleic acid molecule comprising the particular sequence is not essential to the subject disclosure, and may occur by any technique or methodology known to those of skill in the art. For example, a nucleic acid molecule may be introduced by direct transformation methods, such as *Agrobacterium*-mediated transformation of plant tissue; microprojectile bombardment; electroporation; etc. Alternatively, a nucleic acid molecule may be introduced by crossing a plant having the particular nucleotide sequence with another plant, such that progeny have the nucleotide sequence incorporated into their genome. Such breeding techniques are well-known to one skilled in the art. Marker-assisted breeding techniques, as disclosed herein, may greatly facilitate the incorporation of Rf3 through such crosses.

In embodiments wherein the Rf3 gene is introduced to an organism, it may be desirable for the Rf3 gene to be introduced in such a manner that the Rf3 gene is operably linked to one or more regulatory sequences, for example, introduction via the use of a plasmid comprising the Rf3 gene operably linked to the desired regulatory sequences. Regulatory sequences useful in the expression of heterologous nucleic acid sequences are well-known in the art, and include, for example and without limitation: Promoters (e.g., constitutive promoters; tissue-specific promoters; and developmental stage-specific promoters); termination sequences; enhancer sequences; subcellular targeting sequences; stabilizing or leader sequences; and introns.

In some embodiments, the Rf3 gene may be introduced to an organism with one or more additional desirable nucleic acid sequences (for example, genes). Additional desirable nucleic acid sequences may include, for example: Genes encoding foreign proteins; agronomic genes; plant disease resistance genes; genes conferring resistance to a plant pest; genes conferring resistance to an herbicide; and genes that confer or contribute to a value-added trait (e.g., modified fatty acid metabolism; decreased phytate content; and modified carbohydrate composition). Examples of all the aforementioned nucleic acid sequences are known to those of skill in the art.

The Rf3 gene may also be introduced to an organism with one or more marker genes operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes for transformation are well known in the transformation arts and include, for example, genes that code for enzymes that metabolically detoxify a selective chemical agent which may be an antibiotic or an herbicide, or genes that encode an altered target which may be insensitive to the inhibitor. Positive selection methods are also known in the art. Examples of marker genes suitable for use in plant cells may include, for example, and without limitation: The neomycin phosphotransferase II (nptII) gene (Fraley et al. (1983) Proc. Natl. Acad. Sci. USA 80:4803); the hygromycin phosphotransferase gene (Vanden Elzen et al. (1985) Plant Mol. Biol. 5:299); gentamycin acetyl transferase, streptomycin phosphotransferase, aminoglycoside-3'-adenyl transferase, and the bleomycin resistance determinant (See, e.g., Hayford et al. (1988) Plant Physiol. 86:1216; Jones et al. (1987) Mol. Gen. Genet. 210:86); Svab et al. (1990) Plant Mol. Biol. 14:197; and Hille et al. (1986) Plant Mol. Biol. 7:171); selectable marker genes that confer resistance to herbicides, such as glyphosate, glufosinate or bromoxynil (See, e.g., Comai et al. (1985) Nature 317:741-744; Gordon-Kamm et al. (1990) Plant Cell 2:603-618; and Stalker et al. (1988) Science 242:419-423); mouse dihydrofolate reductase (Eichholtz et al. (1987) Somatic Cell Mol. Genet. 13:67); plant 5-enolpyruvylshikimate-3-phosphate synthase (Shah et al. (1986) Science 233:478); plant acetolactate synthase (Charest et al. (1990) Plant Cell Rep. 8:643).

Another class of marker genes suitable for plant transformation employs screening of presumptively transformed plant cells rather than direct genetic selection of transformed cells for resistance to a toxic substance, such as an antibiotic. These genes are particularly useful to quantify or visualize the spatial pattern of expression of a gene in specific tissues, and are frequently referred to as "reporter genes," because they can be fused to a gene or gene regulatory sequence for the investigation of gene expression. Commonly used genes for screening transformed cells include β-glucuronidase (GUS), β-galactosidase, luciferase and chloramphenicol acetyltransferase. See, e.g., Jefferson (1987) Plant Mol. Biol. Rep. 5:387; Teeri et al. (1989) EMBO J. 8:343; Koncz et al. (1987) Proc. Natl. Acad. Sci U.S.A. 84:131; and DeBlock et al. (1984) EMBO J. 3:1681.

Recently, in vivo methods for visualizing GUS activity that do not require destruction of plant tissue have been made available. Molecular Probes publication 2908, Imagene Green™, p. 1-4, 1993; and Naleway et al. (1991) J. Cell Biol. 115:151a. Further, genes encoding Fluorescent Proteins (e.g., GFP, EGFP, EBFP, ECFP, and YFP) have been utilized as markers for gene expression in prokaryotic and eukaryotic cells. See Chalfie et al. (1994) Science 263:802. Fluorescent proteins and mutations of fluorescent proteins may be used as screenable markers.

In some embodiments, the maize Rf3 gene and fragments or segments of the maize Rf3 gene disclosed herein may be used to identify homologous Rf3 gene sequences from organisms other than maize (e.g., by sequence comparison). Sequences from organisms other than maize that are homologous to the maize Rf3 gene may be identified and isolated according to well-known techniques, for example, based on their sequence homology to the Rf3 sequence. For example, all or part of the Rf3 coding sequence may be used as a probe which specifically hybridizes to other sequences present in a population of cloned genomic DNA fragments (i.e., a genomic library) from an organism according to routine techniques. Thus, in some embodiments, the present disclosure includes those nucleotide sequences which specifically hybridize to the Rf3 sequence.

Alternatively, sequences from organisms other than maize that are homologous to the maize Rf3 gene may be identified and isolated by sequence comparison. For example, the complete or partial sequenced genome of an organism may be searched according to routine techniques with the maize Rf3 to identify genes within the genome of the organism that share a high degree of sequence identity with maize Rf3, and are therefore likely Rf3 homologues.

For example, all or part of the maize Rf3 sequence may be used as a "reference sequence." Generally, nucleic acid sequences (e.g., cloned or genomic DNA fragments of a genomic library) that are compared to the reference sequence comprise a "comparison window," which is a specific contiguous segment of the nucleic acid sequence. The comparison window may comprise additions or deletions (i.e., gaps) compared to the reference sequence (which does not comprise additions or deletions) for optimal alignment of the two sequences. The comparison window is typically at least 20 contiguous nucleotides in length, but may be 30, 40, 50, 100, or 200 nucleotides in length, or longer. To avoid a high similarity to the reference sequence due to inclusion of deletions in the polynucleotide sequence comparison window, a "gap penalty" may be introduced to be subtracted from the number of nucleotide matches.

Methods of aligning sequences for comparison are well-known in the art. The determination of percent sequence identity between any two sequences can be accomplished using available mathematical algorithms. Non-limiting examples of such mathematical algorithms are the algorithm of Myers and Miller (1988), CABIOS 4:11-7; the local alignment algorithm of Smith et al. (1981) Adv. Appl. Math. 2:482; the global alignment algorithm of Needleman and Wunsch (1970), J. Mol. Biol. 48:443-53; the search-for-local-alignment method of Pearson and Lipman (1988), Proc. Natl. Acad. Sci. USA 85:2444-8; the algorithm of Karlin and Altschul (1990), Proc. Natl. Acad. Sci. USA 87:2264, and Karlin and Altschul (1993) Proc. Natl. Acad. Sci. USA 90:5873-7.

One of ordinary skill in the art can implement these mathematical algorithms on a computer for comparison of sequences to determine sequence identity, or to search a database comprising a plurality of sequences (e.g., an organism genome database) according to shared sequence identity with a reference sequence. Such implementations include, but are not limited to, CLUSTAL in the PC/Gene program (Intelligenetics, Mountain View, Calif.); and the ALIGN program and GAP, BESTFIT, BLAST, FASTA, and TFASTA in the GCG Wisconsin Genetics Software Package, v. 10 (Accelrys Inc., San Diego, Calif.). Sequence alignments using these programs may be performed using their default parameters. Alternatively, it may be desirable to modify the default parameters in some searches (e.g., altering the value of a gap penalty). The selection of a particular computer implementation of mathematical algorithms for calculation of sequence identity, and the selection of parameter values for use in a selected algorithm, are within the discretion of one of skill in the art.

IV. Methods of Using Rf3 Molecular Markers

Methods of using nucleic acid molecular markers that are linked to or that reside within the Rf3 gene to identify plants with a functional restorer gene for S-type CMS may result in a cost savings for plant developers, because such methods may eliminate the need to cross plants comprising a functional restorer gene with CMS plant lines and then phenotype the progenies of the cross.

Additional markers can be identified as equivalent to any of the exemplary markers named herein (e.g., Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39), for example, by determining the frequency of recombination between the additional marker and an exemplary named marker. Such determinations may utilize an improved method of orthogonal contrasts based on the method of Mather (1931), *The Measurement of Linkage in Heredity*, Methuen & Co., London, followed by a test of maximum likelihood to determine a recombination frequency. Allard (1956) Hilgardia 24:235-78. If the value of the recombination frequency is less than or equal to 0.10 (i.e., 10%) in any maize cultivar, then the additional marker is considered equivalent to the particular reference marker for the purposes of use in the presently disclosed methods.

A means for restoring fertility to CMS-S corn may include a nucleic acid sequence from a plant, the detection of said nucleic acid provides a strong indication that the plant comprising the nucleic acid sequence comprises a functional restorer of CMS-S gene. In some examples, a means for restoring fertility to CMS-S corn is a marker that is linked to (e.g., linked; tightly linked; or extremely tightly linked) or that resides within the Rf3 gene.

A means for identifying corn plants carrying a gene for restoring fertility to CMS-S corn may be a molecule that presents a detectable signal when added to a sample obtained from a plant carrying a gene for restoring fertility to CMS-S corn. Specific hybridization of nucleic acids is a detectable signal, and a nucleic acid probe that specifically hybridizes to a CMS-S restorer gene, or a different genomic nucleic acid sequence that is an indicator of the presence of a functional CMS-S restorer gene, may therefore be a means for identifying corn plants carrying a gene for restoring fertility to CMS-S corn. In some examples, a means for identifying plants carrying a gene for restoring fertility to CMS-S corn is a probe that specifically hybridizes to a marker that is linked to (e.g., linked; tightly linked; or extremely tightly linked) or that resides within the maize Rf3 gene.

In some embodiments, markers flanking the Rf3 gene may be used to transfer segment(s) of donor parent DNA that unequivocally contain the Rf3 gene. In particular embodiments, the markers are selected from the group of markers comprising Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39. In other embodiments, equivalent markers are selected from the group of markers comprising Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39. In some embodiments, a method for using markers flanking the Rf3 gene to transfer segment(s) of donor parent DNA that contain the Rf3 gene may comprise analyzing the genomic DNA of two parent plants with probes that are specifically hybridizable to markers linked (e.g., linked; tightly linked; or extremely tightly linked) to the Rf3 gene; sexually crossing the two parental plant genotypes to obtain a progeny population, and analyzing those progeny for the presence of the markers linked (e.g., linked; tightly linked; or extremely tightly linked) to the Rf3 gene; backcrossing the progeny that contain the markers linked (e.g., linked; tightly linked; or extremely tightly linked) to the Rf3 gene to the recipient genotype to produce a first backcross population, and then continuing with a backcrossing program until a final progeny is obtained that comprises any desired trait(s) exhibited by the parent genotype and the Rf3 gene. In particular embodiments, individual progeny obtained in each crossing and backcrossing step are selected by Rf3 marker analysis at each generation. In some embodiments, analysis of the genomic DNA of the two parent plants with probes that are specifically hybridizable to markers linked (e.g., linked; tightly linked; or extremely tightly linked) to the Rf3 gene reveals that one of the parent plants comprises fewer of the linked markers to which the probes specifically hybridize, or none of the linked markers to which the probes specifically hybridize.

In some embodiments, markers that are linked to (e.g., linked; tightly linked; or extremely tightly linked) or that reside within the maize Rf3 gene, or the maize Rf3 gene sequence itself, may be used to introduce the maize Rf3 gene into a maize plant by genetic transformation. In particular embodiments, the markers are selected from the group of markers comprising Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39. In other embodiments, equivalent markers are selected from the group of markers comprising Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39. In some embodiments, a method for introducing the maize Rf3 gene into a maize plant by genetic recombination may comprise analyzing the genomic DNA of a plant (e.g., a maize plant) with probes that are specifically hybridizable to markers linked (e.g., linked; tightly linked; or extremely tightly linked) to the Rf3 gene or the Rf3 gene itself to identify the Rf3 gene in the plant; isolating a segment of the genomic DNA of the plant comprising the Rf3 gene, for example, by extracting the genomic DNA and digesting the genomic DNA with one or more restriction endonuclease enzymes; optionally amplifying the isolated segment of DNA; introducing the isolated segment of DNA into a cell or tissue of a host maize plant; and analyzing the DNA of the host maize plant with probes that are specifically hybridizable to markers linked (e.g., linked; tightly linked; or extremely tightly linked) to the Rf3 gene or the Rf3 gene itself to identify the Rf3 gene in the host maize plant. In particular embodiments, the isolated segment of DNA may be introduced into the host maize plant such that it is stably integrated into the genome of the host maize plant.

In some embodiments, markers that are linked to (e.g., linked; tightly linked; or extremely tightly linked) or that reside within the maize Rf3 gene, or the maize Rf3 gene sequence itself, may be used to introduce the maize Rf3 gene into other organisms, for example, plants. In particular embodiments, the markers are selected from the group of markers comprising Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39. In other embodiments, equivalent markers are selected from the group of markers comprising Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, and DASCMS-SRf39. In some embodiments, a method for introducing the maize Rf3 gene into an organism other than maize may comprise analyzing the genomic DNA of a plant (e.g., a maize plant) with probes that are specifically hybridizable to markers linked (e.g., linked; tightly linked; or extremely tightly linked) to the Rf3 gene or the Rf3 gene itself to identify the Rf3 gene in the plant; isolating a segment of the genomic DNA of the plant comprising the Rf3 gene, for example, by extracting the genomic DNA and digesting the genomic DNA with one or more restriction endonuclease enzymes; optionally amplifying the isolated segment of DNA; introducing the isolated segment of DNA into an organism other than maize; and analyzing the DNA of the organism other than maize with probes that are specifically hybridizable to markers linked (e.g., linked; tightly linked; or extremely tightly linked) to the Rf3 gene or the Rf3 gene itself to identify the Rf3 gene in the organism. In particular embodiments, the isolated segment of DNA may be introduced into the organism such that it is stably integrated into the genome of the organism.

In some embodiments, markers that are linked to (e.g., linked; tightly linked; or extremely tightly linked) or that reside within the Rf3 gene, or the Rf3 gene sequence itself, may be used to identify a plant with a functional restorer gene for CMS-S male sterility. In particular embodiments, the plant is a maize plant. In some embodiments, nucleic acid molecules (e.g., genomic DNA or mRNA) may be extracted from a plant. The extracted nucleic acid molecules may then be contacted with one or more probes that are specifically hybridizable to markers linked (e.g., linked; tightly linked; or extremely tightly linked) to the Rf3 gene or the Rf3 gene itself. Specific hybridization of the one or more probes to the extracted nucleic acid molecules is indicative of the presence of a functional restorer gene for CMS-S male sterility in the plant.

V. Organisms Comprising the Rf3 Gene

Some embodiments of the present disclosure also provide an organism including a nucleic acid molecule comprising the Rf3 sequence (SEQ ID NO:92), a nucleic acid sequence that is specifically hybridizable to the Rf3 sequence (SEQ ID NO:92), or a functional variant of the Rf3 sequence (SEQ ID NO:92). A suitable organism can be any suitable plant, yeast, or bacterium. By way of non-limiting example, a plant comprising the aforementioned sequences may be a plant of agronomic value, for example and without limitation: maize; soybean; alfalfa; wheat; rapeseed; rice; sorghum; beet; various vegetables including cucumber, tomato, peppers, etc.; various trees including apple, pear, peach, cherry, redwood, pine, oak, etc.; and various ornamental plants. In particular embodiments, the organism may be a sexually-reproducing plant. A seed-bearing plant that comprises a particular nucleic acid sequence may produce seeds that comprise the nucleic acid sequence.

Plant cells comprising the Rf3 sequence (SEQ ID NO:92), a nucleic acid sequence that is specifically hybridizable to the Rf3 sequence (SEQ ID NO:92), or a functional variant of the Rf3 sequence (SEQ ID NO:92), may be cultured and kept as plant tissue culture cells, or certain plant hormones known in the art can be added to the culture media, thereby causing the plant tissue culture cells to differentiate and form a new plant variety, which new plant variety may be fertile or sterile. Such plant culturing methods useful in these and other embodiments are routine and well-known in the art.

Some embodiments of the present disclosure provide a virus (e.g., a bacteriophage, or plant virus) comprising the Rf3 sequence (SEQ ID NO:92), a nucleic acid sequence that is specifically hybridizable to the Rf3 sequence (SEQ ID NO:92), or a functional variant of the Rf3 sequence (SEQ ID NO:92).

VI. Various Embodiments of the Present Disclosure

In one embodiment, a method for selecting a plant comprising a functional restorer gene for maize S-type cytoplasmic male sterility is provided. The method comprises the steps of (a) screening a population of plants for at least one marker nucleic acid, wherein the marker nucleic acid comprises an allele linked to the functional restorer gene for maize S-type cytoplasmic male sterility; (b) detecting the marker nucleic acid; (c) identifying a plant comprising the marker nucleic acid; and (d) selecting the plant comprising the marker nucleic acid, wherein the plant comprising the marker nucleic acid further comprises the functional restorer gene for maize S-type cytoplasmic male sterility. As used herein, the term "marker nucleic acid" means a nucleic acid molecule that is utilized to determine an attribute or feature (e.g., presence or absence, location, correlation, etc.) of a molecule, cell, or tissue.

In some embodiments, the marker nucleic acid comprises a haplotype of alleles linked to the functional restorer gene for maize S-type cytoplasmic male sterility. In other embodiments, the marker nucleic acid is selected from the group consisting of Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, DASCMS-SRf39, and any combination thereof. In yet other embodiments, the marker nucleic acid is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:45, SEQ ID NO:46, SEQ ID NO:47, SEQ ID NO:48, SEQ ID NO:49, SEQ ID NO:50, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85 and any combination thereof.

In some embodiments, the marker nucleic acid is selected from the group consisting of PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, DASCMS-SRf39, and any combination thereof. In other embodiments, the marker nucleic acid is selected from the group consisting of SEQ ID NO:45, SEQ ID NO:46, SEQ ID NO:47, SEQ ID NO:48, SEQ ID NO:49, SEQ ID NO:50, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, and any combination thereof. In yet other embodiments, the marker nucleic acid is selected from the group consisting of CMSS03, CMSS10, CMSS15, CMSS34, DASCMS-SRf31, DASCMS-SRf34, DASCMS-SRf321, DASCMS-SRf39, and any combination thereof. In other embodiments, the marker nucleic acid is selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, and any combination thereof.

In various embodiments, at least one of the markers is associated within 8.3 Mb of the functional restorer gene for maize S-type cytoplasmic male sterility. In other various embodiments, at least one of the markers is associated within 0.5 Mb of the functional restorer gene for maize S-type cytoplasmic male sterility. In yet other various embodiments, at least one of the markers is associated within 100 kb of the functional restorer gene for maize S-type cytoplasmic male sterility.

In some embodiments, the plant is a maize plant. In another embodiment, the maize plant belongs to the Stiff Stalk heterotic group. Maize hybrids, such as temperate maize hybrids, can be derived from a heterotic group such as the Iowa Stiff Stalk heterotic group. The Stiff Stalk heterotic group is well known in the art of plant breeding. In yet another embodiment, the functional restorer gene for maize S-type cytoplasmic male sterility is the Rf3 gene (SEQ ID NO:92). In another aspect of the present disclosure, a maize plant is obtained by the described method.

In yet another aspect of the present disclosure, the method further comprises the steps of (e) obtaining the plant comprising the functional restorer gene for maize S-type cytoplasmic male sterility; (f) crossing the plant comprising the functional restorer gene for maize S-type cytoplasmic male sterility to a second plant to produce one or more progeny plants; (g) evaluating the progeny plant for at least one marker nucleic acid comprising an allele linked to the functional restorer gene for maize S-type cytoplasmic male sterility; and (h) selecting the progeny plant comprising the at least one marker nucleic acid comprising an allele linked to the functional restorer gene for maize S-type cytoplasmic male sterility.

In one embodiment, a method for restoring fertility in a progeny of an S-type cytoplasmic male sterile plant is provided. The method comprises the steps of (a) crossing a female plant with a male plant to generate a population of progeny plants, wherein the female plant is an S-type cytoplasmic male sterile plant, and wherein the male plant possesses a functional restorer gene for S-type cytoplasmic male sterility; (b) screening the population of progeny plants to identify a fertile progeny plant comprising at least one marker nucleic acid comprising an allele linked to the functional restorer gene for maize S-type cytoplasmic male sterility; (c) selecting the fertile progeny plant comprising at least one marker nucleic acid comprising an allele linked to the functional restorer gene for maize S-type cytoplasmic male sterility; and (d) propagating the fertile progeny plant, wherein the fertile progeny plant comprises the functional restorer gene for maize S-type cytoplasmic male sterility.

In some embodiments, the marker nucleic acid comprises a haplotype of alleles linked to the functional restorer gene for maize S-type cytoplasmic male sterility. In other embodiments, the marker nucleic acid is selected from the group consisting of Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, DASCMS-SRf39, and any combination thereof. In yet other embodiments, the marker nucleic acid is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:45, SEQ ID NO:46, SEQ ID NO:47, SEQ ID NO:48, SEQ ID NO:49, SEQ ID NO:50, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85 and any combination thereof.

In some embodiments, the marker nucleic acid is selected from the group consisting of PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, DASCMS-SRf39, and any combination thereof. In other embodiments, the marker nucleic acid is selected from the group consisting of SEQ ID NO:45, SEQ ID NO:46, SEQ ID NO:47, SEQ ID NO:48, SEQ ID NO:49, SEQ ID NO:50, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, and any combination thereof. In yet other embodiments, the marker nucleic acid is selected from the group consisting of CMSS03, CMSS10, CMSS15, CMSS34, DASCMS-SRf31, DASCMS-SRf34, DASCMS-SRf321, DASCMS-SRf39, and any combination thereof. In other embodiments, the marker nucleic acid is selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, and any combination thereof.

In various embodiments, at least one of the markers is associated within 8.3 Mb of the functional restorer gene for maize S-type cytoplasmic male sterility. In other various embodiments, at least one of the markers is associated within 0.5 Mb of the functional restorer gene for maize S-type cytoplasmic male sterility. In yet other various embodiments, at least one of the markers is associated within 100 kb of the functional restorer gene for maize S-type cytoplasmic male sterility.

In some embodiments, the plant is a maize plant. In another embodiment, the maize plant belongs to the Stiff Stalk heterotic group.

In yet another aspect of the present disclosure, the method further comprises the steps of isolating nucleic acid molecules from the population of progeny plants; contacting the isolated nucleic acid molecules with a set of oligonucleotides; and amplifying the isolated nucleic acid molecules and the oligonucleotides to produce an amplicon, wherein the amplicon comprises a detectable signal that is indicative of the presence of the functional restorer gene for maize S-type cytoplasmic male sterility.

In one embodiment, a method for transferring an Rf3 gene into a progeny plant is provided. The method comprises the steps of (a) crossing a first parent plant and a second parent plant to produce a progeny plant, wherein at least one parent plant comprises the Rf3 gene; (b) analyzing the progeny plant for the presence of at least one marker that is linked to the Rf3 gene to obtain an Rf3 progeny plant; (c) backcrossing the Rf3 progeny plant with either the first parent plant or the second parent plant to produce a next-generation progeny plant; and (d) analyzing the next-generation progeny plant for the presence of the at least one marker that is linked to the Rf3 gene to obtain an Rf3 next-generation progeny plant.

In some embodiments, the marker nucleic acid comprises a haplotype of alleles linked to the functional restorer gene for maize S-type cytoplasmic male sterility. In other embodiments, the marker nucleic acid is selected from the group consisting of Mo17-14388, PZE-102180901, PZE-102180129, FG-1318, PZE-102182167, PZE-102182672, PZE-102182718, PZE-102183578, PZE-102183795, DAS-PZ-13844, PZE-102184593, PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, DASCMS-SRf39, and any combination thereof. In yet other embodiments, the marker nucleic acid is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:45, SEQ ID NO:46, SEQ ID NO:47, SEQ ID NO:48, SEQ ID NO:49, SEQ ID NO:50, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85 and any combination thereof.

In some embodiments, the marker nucleic acid is selected from the group consisting of PPR1_P5_1, PPR3_P4_2, PPR8_P6_1, PPR3-5, PPR3-7, PPR3-9, CMSS03, CMSS10, CMSS15, CMSS34, DASCMS-SRf31, DASCMS-SRf34, DASCMS-SRf321, DASCMS-SRf39, and any combination thereof. In other embodiments, the marker nucleic acid is selected from the group consisting of SEQ ID NO:45, SEQ ID NO:46, SEQ ID NO:47, SEQ ID NO:48, SEQ ID NO:49, SEQ ID NO:50, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, and any combination thereof. In yet other embodiments, the marker nucleic acid is selected from the group consisting of CMSS03, CMSS10, CMSS15, CMSS34, DASCMS-SRf31, DASCMS-SRf34, DASCMS-SRf321, DASCMS-SRf39, and any combination thereof. In other embodiments, the marker nucleic acid is selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, and any combination thereof.

In various embodiments, at least one of the markers is associated within 8.3 Mb of the functional restorer gene for maize S-type cytoplasmic male sterility. In other various embodiments, at least one of the markers is associated within 0.5 Mb of the functional restorer gene for maize S-type cytoplasmic male sterility. In yet other various embodiments, at least one of the markers is associated within 100 kb of the functional restorer gene for maize S-type cytoplasmic male sterility.

In some embodiments, the plant is a maize plant. In another embodiment, the maize plant belongs to the Stiff Stalk heterotic group. In yet another embodiment, the Rf3 gene is SEQ ID NO:92.

The following examples are provided to illustrate certain particular features and/or embodiments. The examples should not be construed to limit the disclosure to the particular features or embodiments exemplified.

EXAMPLES

Example 1: Plant Material

A male sterile line of CMS-S type, 4XP811-D (U.S. Pat. No. 7,135,629), and a male sterile restorer line responding to CMS-S type, LH60, were used as parents to generate $F_1$ progeny. The $F_1$ progeny where then selfed to generate an $F_2$ population. The $F_2$ population, consisting of 450 individuals, was used for identification of the Rf3 gene and markers linked (e.g., linked; tightly linked; or extremely tightly linked) to the Rf3 gene.

A $BC_1$ population of 275 individuals derived from 4XP811-D×MBB56, a male sterile restorer line responding to CMS-S type, was used for linkage map analysis with molecular markers designed from the 10 PPR genes within the 1.3 Mb interval.

Example 2: Fertility Classification

The individuals from the $F_2$ and $BC_1$ populations were phenotypically classified according to pollen shed from the tassels. Plants that shed pollen were classified as fertile. Plants that did not shed pollen were classified as sterile. Partial fertile plants were observed in the $F_2$ population but not in the $BC_1$ population.

The individuals from the $BC_1$ population were also phenotypically classified by determining the vitality of pollen grain by using 1% $KI-I_2$ staining. For the fertile plants, the staining results show well stained pollen that were starch-filled and for the sterile plants, the staining results show un-stained collapsed pollen. Table 1 provides the segregation data from the $F_2$ and $BC_1$ mapping populations.

TABLE 1

| Phenotypic segregation data from the $F_2$ and $BC_1$ mapping populations | | | | | | |
|---|---|---|---|---|---|---|
| Population | Size | Fertile plants | Semi-fertile plants | Sterile plants | Non-pollinated plants | Broken plants |
| $F_2$ | 450 | 347 | 73 | 24 | 4 | 2 |
| $BC_1$ | 275 | 139 | 0 | 120 | 0 | 16 |

Example 3: DNA Extraction and Quantification

Genomic DNA was extracted from 8 leaf punches per sample using the MagAttract™ DNA extraction method (Qiagen, Valencia, Calif.) and the Biocel 1800™ (Agilent Technologies, Santa Clara, Calif.). DNA samples were quantified with Quant-iT™ PicoGreen® Quantification Kit (Invitrogen, Carlsbad, Calif.) per manufacturer's instructions or with the Nanodrop 8000 Spectrophotometer™ (Thermo Scientific, Rockford, Ill.) per manufacturer's instructions. The DNA concentration was normalized to 6 ng/µL for use in the KASPar™ genotyping system (KBioscience Inc., Hoddesdon, UK).

Example 4: KASPar™ SNP Genotyping System

The Competitive Allele-Specific PCR genotyping system (KASPar™) is a SNP detection system that uses a technique based on allele-specific oligo extension and fluorescence resonance energy transfer (FRET) for signal generation. Each SNP marker in a KASPar™ assay requires only two components: The assay mix (a mixture of three unlabelled primers: two allele specific oligos, and one common reverse locus specific oligo); and the reaction mix (the other components required for PCR, including the universal fluorescent reporting system and Taq polymerase). Fluorescent signals after the completion of KASPar™ reactions are read in a spectrofluorometer with an excitation wavelength at 485 nm, and an emission wavelength at 535 nm for the FAM fluorophore; and an excitation wavelength at 525 nm, and an emission wavelength at 560 nm for the VIC fluorophore. The data were analyzed using Klustercaller™ software (KBiosciences Inc.) to determine the genotypes of each SNP marker in a population.

The KASPar™ assays based on SNPs or InDels were designed with the Kraken™ workflow manager (KBioSciences, Hoddesdon, Hertfordshire, UK). KASPar™ reactions were set up according to Tables 2 and 3. PCR cycles started at 94° C. for 15 minutes, then 20 cycles with 10 seconds of denature at 94° C. and 5 seconds of annealing at 57° C., then 10 seconds of extension at 72° C., followed by 22 cycles with 10 seconds of denature at 94° C. and 20 seconds of annealing at 57° C., then 40 seconds of extension at 72° C. ABI GeneAmp® PCR System 9700 (Applied Biosystems, Foster City, Calif.) was used for amplification. PCR products were measured by PheraStar™ spectrofluorometer (BMG LABTECH Inc., Cary, N.C.).

TABLE 2

Recipe for assay mix set up

| | Concentration in Assay Mix (µM) | Volume in Assay Mix (µl) |
|---|---|---|
| Allele Specific Primer 1 (A1, 100 µM) | 12 | 12 |
| Allele Specific Primer 2 (A2, 100 µM) | 12 | 12 |
| Common (reverse) Primer (C1, 100 µM) | 30 | 30 |
| H₂0/TrisHCl (10 mM, pH 8.3) | — | 46 |
| TOTAL | | 100 |

TABLE 3

Recipe for KASPar ™ reaction in a 5 µl final volume

| Components | Volume (µl) |
|---|---|
| DNA (5 ng/µl): | 1 |
| 2X Reaction Mix: | 2.5 |
| Assay Mix: | 0.07 |
| *MgCl2 (50 mM): | 0.04 |
| H2O: | 1.39 |
| TOTAL: | 5 |

Example 5: Preliminary Genetic Mapping of Rf3 in the F₂ Population Using SNP Markers JoinMap 4.0™ (Van Ooijen, J. W. et al, 2006) was used to create the genetic linkage map and MapQTL 5.0™ (Van Ooijen, J. W. et al, 2006) was used to map the QTLs in the F₂ population. The interval mapping method was performed. When a LOD score exceeds the significance threshold (permutation test results) on a linkage group, a segregating QTL is detected; the position with the largest LOD on the linkage group is the estimated position of the QTL on the map.

KASPar™ assays were developed for 140 selected SNP markers (one marker per 10 cM for chromosome 2 and per 20 cM for the other chromosomes), and were used to genotype the whole population for linkage map construction and QTL analysis. One hundred thirty-three SNP markers were successfully assigned to 10 linkage groups with a LOD threshold of 3.0.

Figure 1B:
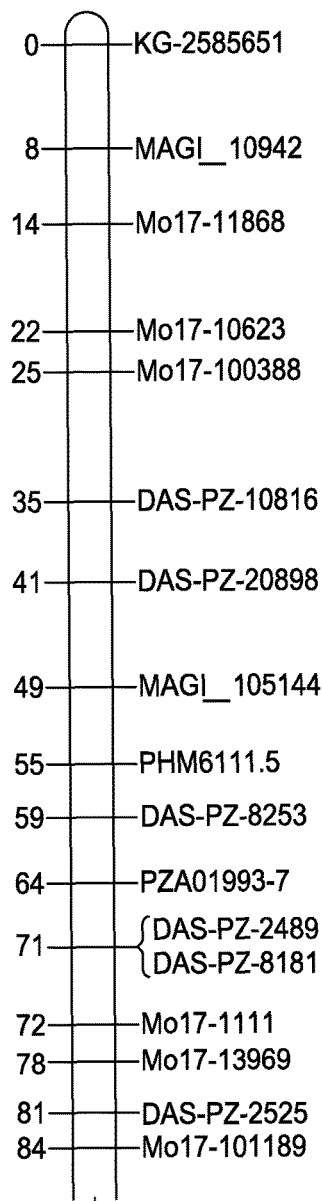
FIG. 1B is a genetic map of chromosome 2, including the CMS-S fertility restorer QTL.
Figure 1B:
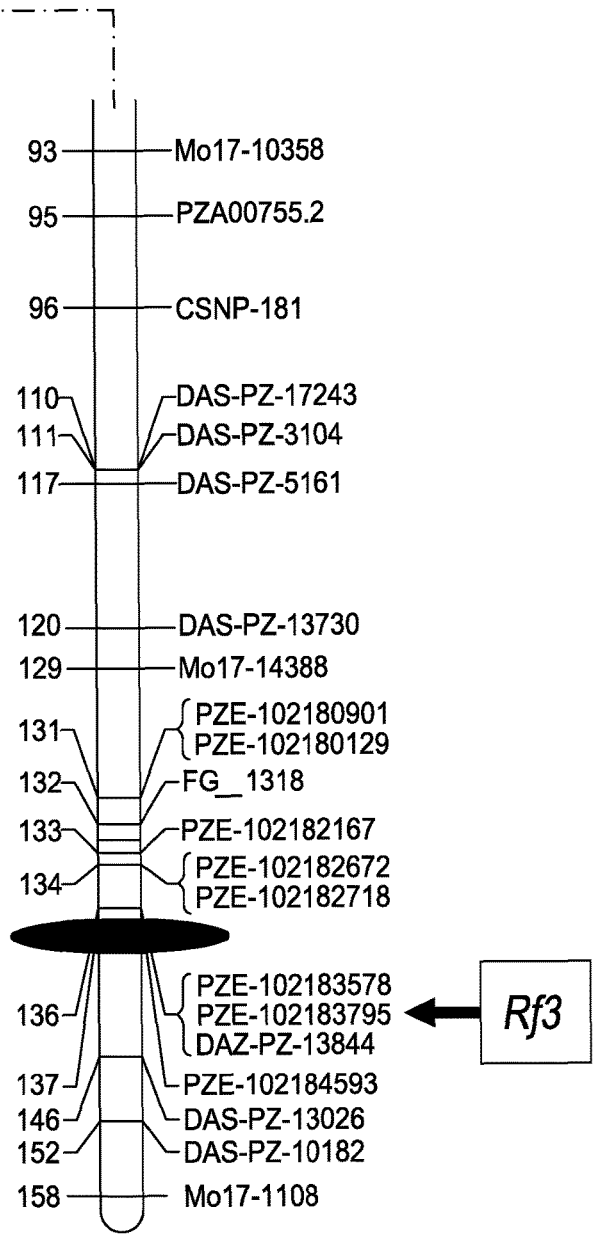

A 3.6 LOD value was set as the significant threshold after running 1000 permutations. Genome-wide QTL analysis detected one significant QTL for restoring the CMS-S fertility of this germplasm (see FIG. 1). The QTL explained 30% of the total phenotypic variation. This QTL was tightly linked to molecular markers Mo17-14388, PZE-102180901, PZE-102180129, FG-1318, PZE-102182167, PZE-102182672, PZE-102182718, PZE-102183578, PZE-102183795, DAS-PZ-13844, and PZE-102184593 within a 8.3 Mb region on chromosome 2, and its location was co-incident with that of the restorer gene Rf3 (see FIG. 1, Table 3).

TABLE 3

Exemplary markers that co-segregate with the Rf3 locus in the 8.3 Mb region on chromosome 2.

| Markers | SEQ ID NO. | Genetic Position (cM) | LOD | Variance | % Expl. | Additive Effect | Allele specific primer 1 SEQ ID NO. | Allele specific primer 2 SEQ ID NO. | Common primer SEQ ID NO. |
|---|---|---|---|---|---|---|---|---|---|
| Mo17-14388 | 1 | 129.25 | 29.5 | 57.46 | 26.6 | −7.09 | 12 | 23 | 34 |
| PZE-102180901 | 2 | 131.14 | 31.83 | 56.08 | 28.1 | −7.36 | 13 | 24 | 35 |
| PZE-102180129 | 3 | 131.47 | 28.85 | 57.85 | 25.9 | −6.94 | 14 | 25 | 36 |
| FG-1318 | 4 | 131.6 | 29.78 | 57.29 | 26.6 | −7.09 | 15 | 26 | 37 |
| PZE-102182167 | 5 | 133.47 | 30.54 | 56.84 | 27.2 | −7.34 | 16 | 27 | 38 |
| PZE-102182672 | 6 | 133.59 | 30.49 | 56.87 | 27.1 | −7.33 | 17 | 28 | 39 |
| PZE-102182718 | 7 | 133.59 | 30.49 | 56.87 | 27.1 | −7.33 | 18 | 29 | 40 |
| PZE-102183578 | 8 | 135.77 | 31.87 | 56.06 | 28.1 | −7.66 | 19 | 30 | 41 |
| PZE-102183795 | 9 | 135.99 | 32.97 | 55.43 | 29 | −7.83 | 20 | 31 | 42 |
| DAS-PZ-13844 | 10 | 136.36 | 32.24 | 55.85 | 28.4 | −7.72 | 21 | 32 | 43 |
| PZE-102184593 | 11 | 136.55 | 29.65 | 57.37 | 26.5 | −7.33 | 22 | 33 | 44 |

Example 6: Annotation of the 8.3 Mb QTL Region

The annotation of the 8.3 Mb QTL region was performed from nucleotide sequence from 220,446,527 bp to 228,748,276 bp, using the *Zea mays* c.v. B73 Reference Genome version 2, which is publically available at such sites as Maize GDB. A total of 142 genes were found in this region (data not show). Ten of the 142 genes were PPR genes (identified with asterisks; ***) (Table 4). These 10 PPR genes were located within a 1,282,382 by interval, where the Rf3 gene was mapped. Some of PPRs matched known restorer genes from some previous studies, and could be Rf3 candidate genes.

TABLE 4

Results of the annotation of the 8.3 Mb QTL region. Ten PPR genes were identified in the region. The PPR genes are identified with asterisks; ***.

| Chr | Start | Stop | Gene |
|---|---|---|---|
| Chr2 | 226676462 | 226678841 | Pentatricopeptide repeat *** |
| Chr2 | 226679089 | 226680887 | Bifunctional inhibitor/plant lipid transfer protein/seed storage |
| Chr2 | 226699977 | 226705433 | BTB/POZ-like |
| Chr2 | 226699977 | 226705433 | Tetratricopeptide region |
| Chr2 | 226699977 | 226705433 | BTB/POZ fold |
| Chr2 | 226699977 | 226705433 | Tetratricopeptide TPR-1 |
| Chr2 | 226963057 | 227123377 | Serine/threonine protein kinase |
| Chr2 | 226963057 | 227123377 | Serine/threonine protein kinase, active site |
| Chr2 | 226963057 | 227123377 | Protein kinase-like |
| Chr2 | 226963057 | 227123377 | Serine/threonine protein kinase |
| Chr2 | 226963057 | 227123377 | Protein kinase-like |
| Chr2 | 226963057 | 227123377 | Protein kinase-like |
| Chr2 | 227029696 | 227031991 | Homeobox |
| Chr2 | 227029696 | 227031991 | Homeodomain-like |
| Chr2 | 227045894 | 227046871 | Pentatricopeptide repeat *** |
| Chr2 | 227209438 | 227212064 | Pentatricopeptide repeat *** |
| Chr2 | 227213495 | 227214494 | Protein kinase-like |
| Chr2 | 227264500 | 227268560 | Helix-loop-helix DNA-binding |
| Chr2 | 227264500 | 227268560 | Cyclin-like |
| Chr2 | 227264500 | 227268560 | Basic helix-loop-helix dimerisation region bHLH |
| Chr2 | 227277494 | 227282413 | Kelch |
| Chr2 | 227277494 | 227282413 | Galactose oxidase/kelch, beta-propeller |
| Chr2 | 227277494 | 227282413 | Kelch repeat type 1 |
| Chr2 | 227516080 | 227537665 | Protein kinase-like |
| Chr2 | 227544895 | 227545712 | Histone H2A |
| Chr2 | 227544895 | 227545712 | Histone-fold |
| Chr2 | 227544895 | 227545712 | Histone core |
| Chr2 | 227586065 | 227587703 | Pentatricopeptide repeat *** |
| Chr2 | 227599623 | 227600372 | Pentatricopeptide repeat *** |
| Chr2 | 227604054 | 227608803 | Pentatricopeptide repeat *** |
| Chr2 | 227610560 | 227618077 | DNA topoisomerase I, C-terminal |
| Chr2 | 227610560 | 227618077 | DNA breaking-rejoining enzyme, catalytic core |
| Chr2 | 227618518 | 227619348 | Pentatricopeptide repeat *** |
| Chr2 | 227652480 | 227654480 | Protein kinase-like |
| Chr2 | 227657388 | 227658767 | Histone H2A |
| Chr2 | 227657388 | 227658767 | Histone-fold |
| Chr2 | 227657388 | 227658767 | Histone core |
| Chr2 | 227876866 | 227880456 | Pentatricopeptide repeat *** |
| Chr2 | 227882663 | 227886563 | Antifreeze protein, type I |
| Chr2 | 227882663 | 227886563 | Antifreeze protein, type I |
| Chr2 | 227893366 | 227895004 | Pentatricopeptide repeat *** |
| Chr2 | 227932245 | 227946984 | Histone H2A |
| Chr2 | 227932245 | 227946984 | Histone-fold |
| Chr2 | 227932245 | 227946984 | Histone core |
| Chr2 | 227955470 | 227957312 | Protein kinase-like |
| Chr2 | 227958844 | 227962673 | Pentatricopeptide repeat *** |

Example 7: Fine Mapping the Rf3 Gene to a 1.3 Mb Region on Chromosome 2

After the PPR genes were identified based on the annotation of the QTL region in B73 reference genome, homolog sequences from CMS-S line 4XP811-D and restorer line LH60 were generated using PCR with specific primers which were designed based on the PPR gene sequences in B73. The PCR was performed in total volumes of 50 μl containing 100 ng of genomic DNA, 10× Qiagen™ PCR buffer, 25 mM MgCl$_2$, 2.5 mM of each dNTP, 0.25 mM of specific primers, and 5 U Taq plus polymerase. The PCR conditions for specific primers were 2-minutes initial denaturation at 94° C., followed by 7 cycles of 98° C. for 10 seconds, 62° C. with −1.0° C. touchdown for 20 seconds and 72° C. for 4 minutes 30 seconds, then followed by 25 cycles of 98° C. for 10 seconds, 56° C. for 20 seconds and 72° C. for 4 minutes 30 seconds, with a final extension at 72° C. for 10 minutes. PCR products were separated by 2% agarose e-gels and purified using a Qiagen DNA purification Kit™ (Qiagen, Germantown, Md.). The purified amplicons were cloned and sequenced by Eurofins MWG Operon (Huntsville, Ala.).

Since the PPR genes contain many repeat sequences, only a few PCR products were obtained from several primer sets that were designed to isolate PPR genes. Sequences from PCR products were aligned with Sequencher 4.10.1™ software (Gene Codes, Ann Arbor, Mich.) between the CMS-S and restorer lines. Variations were identified in the aligned sequences and KASPar™ assays were designed to detect these variations. Six SNP markers polymorphic between parental lines 4XP811-D and LH60 are shown in Table 5.

TABLE 5

Polymorphic markers developed from several PPR genes

| Marker | SNP | SEQ ID NO. | Allele specific primer 1 SEQ ID NO. | Allele specific primer 2 SEQ ID NO. | Common primer SEQ ID NO. |
|---|---|---|---|---|---|
| PPR1_P5_1 | G/C | 45 | 51 | 57 | 63 |
| PPR3_P4_2 | T/— | 46 | 52 | 58 | 64 |
| PPR8_P6_1 | A/G | 47 | 53 | 59 | 65 |
| PPR3-5 | A/G | 48 | 54 | 60 | 66 |
| PPR3-7 | T/— | 49 | 55 | 61 | 67 |
| PPR3-9 | G/A | 50 | 56 | 62 | 68 |

An F2 mapping population 4XP811-D×LH60 was used to map the six polymorphic markers with JoinMap 4.0 software. This population was used to primarily identify the Rf3 restorer gene location on the long arm of chromosome 2. The map contained 133 markers, which were evenly distributed on the whole maize genome and the QTL was well defined and confirmed. Six markers, PPR1_P5_1, PPR3-5, PPR3-7, PPR3-9, PPR8_P6-1, and PPR3_P4_2, were mapped in the peak region with highest LOD scores of the mapped QTL, which was 1.3 Mb in length.

Example 9: Whole Genome Sequencing and Gene-Specific Marker Development

To further identify the specific Rf3 restorer gene sequence and the gene sequence of the rf3 mutation, which results in cytoplasmic male sterility, a whole genome sequencing approach was utilized. The two CMS-S lines, 4XP811-D and 7SH382ms, and the two restorer lines, LH60 and MBB56, were used for sequencing analysis.

A total of 10 PPR genes (annotated sequentially as PPR 1-10) were identified on chromosome 2 within a 1.3 Mb genomic interval after comparison of the sequenced genomic regions with annotated sequence of the reference genome from *Zea mays* c.v. B73 (available at Maize GDB). A full length coding sequence that corresponds with PPR2 did not exist in the annotated B73 genome and could not be predicted as a full length, functional gene. As a result, the full gene sequence for PPR2 was obtained from a sequence comparison to the reference genome of *Zea mays* c.v. Mo17 (available at Maize GDB). The resulting sequences for the 10 PPR genes (PPR2 had two sequences, the first sequence from line B73 and the second sequence from line Mo17) were assembled for reference sequence information based on whole genome sequencing data of the two CMS-S lines and two restorer lines.

Next, the sequences were aligned between CMS-S lines, restorer lines, and the reference genomic sequences for all of the PPR genes. Any genomic sequence variations were identified from the aligned genomic sequences of the PPR genes and noted.

Based on sequences of 10 PPR gene segments, 58 PCR primer pairs were designed and used to screen CMS-S and restorer lines. Only four primer sets (Table 6) from PPR2 showed polymorphisms, which suggested that PPR2 was associated with fertility restoration.

Based on the variations within the PPR2 gene, 21 KASPar™ assays were developed and screened on the BC$_1$ mapping population, and three assays showed polymorphisms between the parental lines (Table 6).

TABLE 6

Polymorphic molecular markers from the PPR2 gene

| Marker | Marker Type | SNP | Primer 1 SEQ ID NO. | Primer 2 SEQ ID NO. | Primer 3 SEQ ID NO. |
|---|---|---|---|---|---|
| CMSS03 | PCR on e-gel | T/C | 69 | 70 | n/a |
| CMSS10 | PCR on e-gel | T/G | 71 | 72 | n/a |
| CMSS15 | PCR on e-gel | T/A | 73 | 74 | n/a |
| CMSS34 | PCR on e-gel | T/G | 75 | 76 | n/a |
| DASCMS-SRf31 | KASPar™ | T/G | 77 | 80 | 83 |
| DASCMS-SRf34 | KASPar™ | C/G | 78 | 81 | 84 |
| DASCMS-SRf321 | KASPar™ | T/C | 79 | 82 | 85 |

Example 10: PPR2 Gene Specific Markers Co-Segregate with Rf3 on Linkage Map

The BC₁ mapping population was genotyped using KAS-Par™ assays with 482 SNP markers, which were evenly distributed on the whole genome. Four hundred and thirty-seven markers (including 4 PCR-based markers from PPR2, 432 SNP markers across the genome, and 1 marker based on sterile-fertile phenotype of the BC$_1$ mapping population) were used to create a genetic linkage with JoinMap 4.0™ software. With the genetic linkage map, phenotypic data and genotypic data, a whole genome QTL analysis was performed using MapQTL 6.0™ software (Kyazma B.V., Netherlands). The results showed that all of the PPR2 gene specific markers (Tables 5 and 6) co-segregated with the Rf3 locus at a genetic position of 177.08 cM, a LOD of 99.99, and explaining 100% of the phenotypic variation.

Example 11: Putative Rf3 Candidate Mutations and Expression Analysis of the Gene Coding PPR2 Protein by Real-Time PCR To validate whether the expression of the Rf3-PPR2 protein is correlated with fertility restoration of CMS-S maize, a real-time PCR (RT-PCR) was performed to quantitatively determine the expression pattern of the Rf3-PPR2 gene in fertile plants and the rf3-PPR2 gene in CMS plants. Several specific primer pairs and probes were designed based on portions of the polynucleotide sequences that contained amino acids with variations in the Rf3-PPR2 protein coding gene. Total RNA was extracted from two lines, 4XP811-D (cytoplasmic male sterile) and LH60 (restorer line), F3 individuals derived from an F2 ear segregating for the 1.3 Mb region of long arm chromosome 2, and three commercial maize lines.

The plants to be analyzed via the Taqman® assay were grown in a greenhouse. Leaf tissues were collected from 7 week (just before tasselling) and 10 week old plants (after pollination). Tassel tissues with developing anthers/pollens and shed pollens (in fertile plants) were also collected. Total RNA was extracted using Qiagen RNeasy Plant Mini Kit™ and cDNA was synthesized using Qiagen QuantiTect Reverse Transcription Kit™ (Qiagen, Carlsbad, Calif.). The expression levels were quantitated by comparison to a maize internal control gene, elongation factor α-1 (EF α1). (Czechowski T, et al., Plant Physiol., September; 139(1):5-17, 2005). Primers for Rf3-PPR2 and EF α1 and dual labeled probes with FAM or VIC dyes and Minor Groove Binding Non Fluorescence Quencher™ I (MGBNFQ) quencher were synthesized by Applied Biosystems (Foster City, Calif.). Taqman® genotyping master mix (Applied Biosystems, Foster City, Calif.) was used to set up 10 µl PCR reactions and the PCR was performed on Roche LightCycler 480™ thermocycler (Roche, Indianapolis, Ind.). The PCR program was initiated with 10 minutes activation of the Taq enzyme at 95° C., followed by 50 cycles of 95° C. for 10 seconds and 58° C. for 38 seconds. Fluorescence signals were recorded at the end of each cycle. Relative expression levels of Rf3-PPR2 to EF α1 was calculated using the Delta Delta CT method.

Seven Taqman® assays were designed based on mutations that resulted in amino acid changes within the Rf3-PPR2 gene. Only the DASCMS-SRf39 assay amplified an amplicon that corresponded with the presence of Rf3 or rf3 gene sequence in the fertile restorer lines and cytoplasmic male sterile lines, respectively (Table 7). This assay was able to identify a single mutation that resulted in the rf3 cytoplasmic male sterile phenotype. As such, this single mutation could be used to discern between the rf3 cytoplasmic male sterile and the Rf3 restored fertile plants. Interestingly, Rf3 expression levels were distinguishable between Rf3 homozygous (Rf3/Rf3) and heterozygous (Rf3/rf3) F3 individuals, which could explain why homozygous (Rf3/Rf3) plants shed 100% starched-filled fertile pollen while heterozygous (Rf3/rf3) plants shed approximately 50% starch-filled fertile pollen. Finally, the Rf3-PPR2 gene, which restores S-type CMS cytoplasm, is expressed in both tassel tissue containing immature pollen, and leaf tissue.

TABLE 7

Primers and probes used for the DASCMS-SRf39 RT-PCR assay and EF α1 internal control.

| Reaction | Primer Name | Primer Sequence | SEQ ID NO: |
|---|---|---|---|
| Rf3 allele specific: DASCMS-SRf39 | Forward Primer | GTACTCATGGTAGTTTACTGAAAGCCA | 86 |
| | Reverse Primer | GCATCCATTACCCTTCCCAAT | 87 |
| | Probe | ATCTTGACATTGTTTTATTCAGTTCG | 88 |
| Internal Control: Elongation Factor α-1 | Forward Primer | ATAACGTGCCTTGGAGTATTTGG | 89 |
| | Reverse Primer | TGGAGTGAAGCAGATGATTTGC | 90 |
| | Probe | TTGCATCCATCTTGTTGC | 91 |

What is claimed is:

1. A method for restoring fertility in a maize plant, the method comprising the steps of:
   (a) crossing a female maize plant with a male maize plant to generate a population of progeny maize plants, wherein the female maize plant is an S-type cytoplasmic male sterile maize plant, and wherein the male maize plant possesses a functional Rf3 restorer gene for S-type cytoplasmic male sterility;
   (b) screening the population of progeny maize plants to identify a fertile progeny maize plant comprising marker nucleic acid Mo17-14388 comprising an allele linked to the functional Rf3 restorer gene for maize S-type cytoplasmic male sterility by extracting nucleic acids from the progeny plants and detecting the marker nucleic acid Mo17-14388;
   (c) selecting the fertile progeny maize plant comprising the marker nucleic acid Mo17-14388 comprising the allele linked to the functional Rf3 restorer gene for maize S-type cytoplasmic male sterility; and
   (d) propagating the fertile progeny maize plant, wherein the fertile progeny maize plant comprises the functional Rf3 restorer gene for maize S-type cytoplasmic male sterility.

2. A method for restoring fertility in a maize plant, the method comprising the steps of:
   (a) crossing a female maize plant with a male maize plant to generate a population of progeny maize plants, wherein the female maize plant is an S-type cytoplasmic male sterile maize plant, and wherein the male maize plant possesses a functional Rf3 restorer gene for S-type cytoplasmic male sterility;
   (b) screening the population of progeny maize plants to identify a fertile progeny maize plant comprising marker nucleic acid DASCMS-SRf39 comprising an allele linked to the functional Rf3 restorer gene for maize S-type cytoplasmic male sterility by extracting nucleic acids from the progeny plants and detecting the marker nucleic acid DASCMS-SRf39;
   (c) selecting the fertile progeny maize plant comprising the marker nucleic acid DASCMS-SRf39 comprising the allele linked to the functional Rf3 restorer gene for maize S-type cytoplasmic male sterility; and
   (d) propagating the fertile progeny maize plant, wherein the fertile progeny maize plant comprises the functional Rf3 restorer gene for maize S-type cytoplasmic male sterility.

3. The method of claim 1, wherein the marker nucleic acid Mo17-14388 is selected from the group consisting of SEQ ID NO: 1, SEQ ID NO: 12, and SEQ ID NO: 23, and any combination thereof.

4. The method of claim 2, wherein the marker nucleic acid DASCMS-SRf39 is selected from the group consisting of SEQ ID NO: 86, SEQ ID NO: 87, and SEQ ID NO: 88, and any combination thereof.

5. The method of claim 1, wherein the marker nucleic acid Mo17-14388 is located on chromosome 2 within 8.3 Mb of the functional Rf3 restorer gene for maize S-type cytoplasmic male sterility.

6. The method of claim 1, the method further comprising introducing the functional Rf3 restorer gene for maize S-type cytoplasmic male sterility into the male plant.

7. The method of claim 6, wherein the introducing is selected from the group consisting of transformation, crossing, backcrossing, homologous recombination, and mutagenesis.

8. The method of claim 1, wherein the progeny maize plant is a hybrid maize plant.

9. The method of claim 8, wherein the hybrid maize plant belongs to the Stiff Stalk heterotic group.

10. The method of claim 1, said screening comprising the steps of:
    isolating nucleic acid molecules from the population of progeny maize plants;
    contacting the isolated nucleic acid molecules with a set of oligonucleotides; and
    amplifying the isolated nucleic acid molecules and the oligonucleotides to produce an amplicon, wherein the amplicon comprises a detectable signal that is indicative of the presence of the functional Rf3 restorer gene for maize S-type cytoplasmic male sterility.

11. The method of claim 6, wherein the functional Rf3 restorer gene for maize S-type cytoplasmic male sterility consists essentially of SEQ ID NO: 92.

12. The method of claim 11, wherein the functional Rf3 restorer gene for maize S-type cytoplasmic male sterility is comprised in an organism selected from the group consisting of a plant, a yeast, a bacterium, and a virus.

13. The method of claim 12, wherein the functional Rf3 restorer gene for maize S-type cytoplasmic male sterility is comprised in a plant cell.

14. The method of claim 9, wherein the female maize plant or the male maize plant of the hybrid maize plant belongs to the Stiff Stalk heterotic group.

15. The method of claim 2, wherein the marker nucleic acid DASCMS-SRf39 is located on chromosome 2 within 8.3 Mb of the functional Rf3 restorer gene for maize S-type cytoplasmic male sterility.

16. The method of claim 2, wherein the marker nucleic acid DASCMS-SRf39 is located on chromosome 2 within 1.3 Mb of the functional Rf3 restorer gene for maize S-type cytoplasmic male sterility.

17. The method of claim 2, wherein the marker nucleic acid DASCMS-SRf39 is located on chromosome 2 within 0.5 Mb of the functional Rf3 restorer gene for maize S-type cytoplasmic male sterility.

18. The method of claim 2, wherein the marker nucleic acid DASCMS-SRf39 is located on chromosome 2 within 100 kb of the functional Rf3 restorer gene for maize S-type cytoplasmic male sterility.

19. The method of claim 2, the method further comprising introducing the functional Rf3 restorer gene for maize S-type cytoplasmic male sterility into the male plant.

20. The method of claim 19, wherein the introducing is selected from the group consisting of transformation, crossing, backcrossing, homologous recombination, and mutagenesis.

21. The method of claim 2, wherein the progeny maize plant is a hybrid maize plant.

22. The method of claim 21, wherein the hybrid maize plant belongs to the Stiff Stalk heterotic group.

23. The method of claim 2, said screening comprising the steps of:
isolating nucleic acid molecules from the population of progeny maize plants;
contacting the isolated nucleic acid molecules with a set of oligonucleotides; and
amplifying the isolated nucleic acid molecules and the oligonucleotides to produce an amplicon, wherein the amplicon comprises a detectable signal that is indicative of the presence of the functional Rf3 restorer gene for maize S-type cytoplasmic male sterility.

24. The method of claim 19, wherein the functional Rf3 restorer gene for maize S-type cytoplasmic male sterility consists essentially of SEQ ID NO: 92.

25. The method of claim 24, wherein the functional Rf3 restorer gene for maize S-type cytoplasmic male sterility is comprised in an organism selected from the group consisting of a plant, a yeast, a bacterium, and a virus.

26. The method of claim 25, wherein the functional Rf3 restorer gene for maize S-type cytoplasmic male sterility is comprised in a plant cell.

27. The method of claim 22, wherein the female maize plant or the male maize plant of the hybrid maize plant belongs to the Stiff Stalk heterotic group.

\* \* \* \* \*